United States Patent
Morgan et al.

(10) Patent No.: US 7,476,512 B2
(45) Date of Patent: Jan. 13, 2009

(54) METHODS OF IDENTIFYING DERMAL PAPILLA CELLS

(75) Inventors: Bruce A. Morgan, Lexington, MA (US); David Enshell-Seijffers, Moshav Avichail (IL)

(73) Assignee: The General Hospital Corporation, Boston, MA (US)

( * ) Notice: Subject to any disclaimer, the term of this patent is extended or adjusted under 35 U.S.C. 154(b) by 316 days.

(21) Appl. No.: 11/067,811

(22) Filed: Feb. 28, 2005

(65) Prior Publication Data

US 2005/0260688 A1 Nov. 24, 2005

Related U.S. Application Data

(60) Provisional application No. 60/548,272, filed on Feb. 27, 2004.

(51) Int. Cl.
*G01N 33/53* (2006.01)
*G01N 33/532* (2006.01)
*G01N 33/563* (2006.01)
*C12N 9/00* (2006.01)

(52) U.S. Cl. .................. 435/7.21; 435/7.1; 435/183

(58) Field of Classification Search ............ None
See application file for complete search history.

(56) References Cited

U.S. PATENT DOCUMENTS

| | | | |
|---|---|---|---|
| 5,208,145 | A | 5/1993 | Rogers |
| 5,460,939 | A | 10/1995 | Hansbrough et al. |
| 5,686,289 | A | 11/1997 | Humes et al. |
| 6,159,950 | A | 12/2000 | Crystal et al. |
| 6,485,972 | B1 | 11/2002 | McMahon et al. |
| 6,924,141 | B2 | 8/2005 | Morgan et al. |
| 2003/0223976 | A1 | 12/2003 | Pan et al. |
| 2004/0170611 | A1 | 9/2004 | Morgan et al. |
| 2004/0171145 | A1 | 9/2004 | Jorcano Noval et al. |

FOREIGN PATENT DOCUMENTS

| | | |
|---|---|---|
| EP | 0405656 | 1/1991 |
| EP | 0451903 | 10/1991 |
| JP | 08-066183 A | 3/1996 |
| WO | WO 95/17416 | 6/1995 |
| WO | WO 97/17982 | 5/1997 |
| WO | WO 99/01034 | 1/1999 |
| WO | WO 99/42481 | 8/1999 |
| WO | WO 99/64608 | 12/1999 |
| WO | WO 00/31134 | 6/2000 |
| WO | WO 01/57194 | 8/2001 |
| WO | WO 01/74164 | 10/2001 |
| WO | WO 02/062135 | 8/2002 |
| WO | WO 03/106657 | 12/2003 |

OTHER PUBLICATIONS

Langenickel et al., Rat corin gene: molecular cloning and reduced expression in experimental heart failure. Am. J. Physiol. Heart Circ. Physiol. 2004.*
Arias et al., "Wnt signaling: pathway or network?" *Curr. Opin. Genet. Dev.*, 9:447-454 (1999).
Bannasch et al., "Skin tissue engineering," *Clin. Plast. Surg.*, 30:573-579 (2003).
Charpentier et al., "Plakoglobin Suppresses Epithelial Proliferation and Hair Growth In Vivo," *J. Cell. Biol.*, 149(2):503-519 (2000).
Christiansen et al., "Murine *Wnt*-11 and *Wnt*-12 have temporally and spatially restricted expression patterns during embryonic development," *Mech. Dev.*, 51:341-350 (1995).
Chuong et al., "Early Events During Avian Skin Appendage Regeneration: Dependence on Epithelial-Mesenchymal Interaction and Order of Molecular Reappearance," *J. Invest. Dermatol.*, 107:639-646 (1996).
Cunliffe et al., "Complete rescue of the nude mutant phenotype by a wild-type *Foxn1* transgene," *Mamm. Genome*, 13:245-252 (2002).
DasGupta and Fuchs, "Multiple roles for activated LEF/TCF transcription complexes during hair follicle development and differentiation," *Development*, 126:4557-4568 (1999).
Gat et al., "De Novo Hair Follicle Morphogenesis and Hair Tumors in Mice Expressing a Truncated β-Catenin in Skin," *Cell*, 95:605-614 (1998).
Gavin et al., "Expression of multiple novel *Wnt*-1/*int*-1-related genes during fetal and adult mouse development," *Genes Dev.*, 4:2319-2332 (1990).
van Genderen et al., "Development of several organs that require inductive epithelial-mesenchymal interactions is impaired in *LEF-1*-deficient mice," *Genes Dev.*, 8:2691-2703 (1994).
Golub et al., "Molecular Classification of Cancer: Class Discovery and Class Prediction by Gene Expression Monitoring," *Science*, 286:531-537 (1999).
Goodrich et al., "Conservation of the *hedgehog/patched* signaling pathway from flies to mice: induction of a mouse *patched* gene by a Hedgehog," *Genes Dev.*, 10:301-312 (1996).
Hardy, "The secret life of the hair follicle," *Trends in Genetics*, 8(2):55-61 (1992).
Hooper et al., "Localizaetion of the mosaic transmembrane serine protease corin to heart myocytes," *Eur. J. Biochem.*, 267:6931-6937 (2000).
Hooper et al., "Type II Transmembrane Serine Proteases," *J. Biol. Chem.*, 276(2):857-860 (2001).
Jahoda et al., "Induction of hair growth by implantation of cultured dermal papilla cells," *Nature*, 311:560-562 (1984).
Kengaku et al., "Distinct WNT Pathways Regulating AER Formation and Dorsoventral Polarity in the Chick Limb Bud," *Science*, 280:1274-1277 (1998).
Kishimoto et al., "Selective activation of the versican promoter by epithelial-mesenchymal interactions during hair follicle development," *Proc. Natl. Acad. Sci. USA*, 96:7336-7341 (1999).
Kishimoto et al., "Wnt signaling maintains the hair-inducing activity of the dermal papilla," *Genes Dev*, 14:1181-1185 (2000).

(Continued)

*Primary Examiner*—Ruixiang Li
(74) *Attorney, Agent, or Firm*—Fish & Richardson P.C.

(57) ABSTRACT

Methods and compositions for identifying and isolating dermal papilla cells are described. DP cells can be identified based on corin expression. Isolated DP cells can be used, e.g., to modulate hair growth.

10 Claims, 2 Drawing Sheets

OTHER PUBLICATIONS

Kitamoto et al., "Enterokinase, the initiator of intestinal digestion, is a mosaic protease composed of a distinctive assortment of domains," *Proc. Natl. Acad. Sci. USA*, 91:7588-7592 (1994).

Lee et al., "Insertional mutagenesis identifies a member of the *Wnt* gene family as a candidate oncogene in the mammary epithelium of *int-2/Fgf-3* transgenic mice," *Proc. Natl. Acad. Sci. USA*, 92:2268-2272 (1995).

Leytus et al., "A Novel Trypsin-like Serine Protease (Hepsin) with a Putative Transmembrane Domain Expressed by Human Liver and Hepatoma Cells," *Biochem.*, 27:1067-1074 (1988).

Magerl et al., "Simple and rapid method to isolate and culture follicular papillae from human scalp hair follicles," *Exp. Dermatol.*, 11:381-385 (2002).

Marigo et al., "Conservation in *hedgehog* signaling: induction of a chicken *patched* homolog by *Sonic hedgehog* in the developing limb," *Development*, 122:1225-1233 (1996).

Messenger, "The culture of dermal papilla cells from human hair follicles," *British J. of Dermatol.*, 110:685-689 (1984).

Millar et al., "WNT Signaling in the Control of Hair Growth and Structure," *Developmental Biology*, 207:133-149 (1999).

Noramly et al., "β-catenin signaling can initiate feather bud development," *Development*, 126:3509-3521 (1999).

Nusse and Varmus, "*Wnt* Genes," *Cell*, 69:1073-1087 (1992).

Oro and Scott, "Splitting Hairs: Dissecting Roles of Signaling Systems in Epidermal Development," *Cell*, 95:575-578 (1998).

Pan et al., "Genomic Structures of the Human and Murine Corin Genes and Functional GATA Elements in Their Promoters," *J. Biol. Chem.*, 277(41):38390-38398 (2002).

Pennisi, "Hairy Mice Offer Hope for Baldness Remedy," *Science*, 282:1617 (1998).

Riddle et al., "Induction of the LIM Homeobox Gene *Lmxl* by WNT7a Established Dorsoventral Pattern in the Vertebrate Limb," *Cell*, 83:631-640 (1995).

Sato et al., "Induction of the hair growth phase in postnatal mice by localized transient expression of Sonic hedgehog," *J. Clin. Invest.*, 104(7):855-864 (1999).

St-Jacques et al., "Sonic hedgehog signaling is essential for hair development," *Curr. Biol.*, 8:1058-1068 (1998).

Tomita et al., "A Novel Low-Density Lipoprotein Receptor-Related Protein with Type II Membrane Protein-Like Structure Is Abundant in Heart," *J. Biochem.*, 124:784-789 (1998).

van't Veer et al., "Molecular Cloning and Chromosomal Assignment of the Human Homolog of *int-1*, a Mouse Gene Implicated in Mammary Tumorigenesis," *Mol. Cell. Biol.*, 4(11):2532-2534 (1984).

Wainwright et al., "Isolation of a human gene with protein sequence similarity to human and murine int-1 and the *Drosophila* segment polarity mutant *wingless*," *EMBO J.*, 7(6):1743-1748 (1988).

Wu, "Gene targeting in hemostasis. hepsin," *Front. Biosci.*, 6:d192-200 (2001).

Wu et al., "Processing of Pro-atrial Natriuretic Peptide by Corin in Cardiac Myocytes," *J. Biol. Chem.*, 277(19):16900-16905 (2002).

Yan et al., "Corin, a Mosaic Transmembrane Serine Protease Encoded by a Novel cDNA from Human Heart," *J. Biol. Chem.*, 274(21):14926-14935 (1999).

Yan et al., "Corin, a transmembrane cardiac serine protease, acts as a pro-atrial natriuretic peptide-converting enzyme," *Proc. Natl. Acad. Sci. USA*, 97(15):8525-8529 (2000).

\* cited by examiner

METHODS OF IDENTIFYING DERMAL PAPILLA CELLS

CROSS-REFERENCE TO RELATED APPLICATIONS

This application claims priority to U.S. application Ser. No. 60/548,272, filed on Feb. 27, 2004, the contents of which are incorporated by reference in their entirety.

BACKGROUND

The hair follicle undergoes a cycle of hair growth (anagen) followed by regression (catagen), and quiescence (telogen) until a new hair shaft is generated in the existing follicle during the subsequent anagen phase (Hardy et al. (1992) Trends Genet. 8:55-61). The hair shaft is derived from the epithelial matrix cells at the base of the follicle, but a cluster of dermal cells ensheathed by the matrix cells, known as the dermal papilla (DP), is thought to supply inductive signals required for hair outgrowth.

SUMMARY

The present application is based, in part, on the discovery that corin is specifically expressed in dermal papilla (DP) cells of the skin. Therefore, corin is identified as a target useful in, inter alia, methods and compositions for identifying and isolating DP cells, for identifying agents that modulate hair growth, and for diagnosing and treating hair growth-related conditions.

Accordingly, in one aspect, this disclosure features a method of identifying a DP cell (e.g., in skin). The method includes evaluating corin expression, levels or activity in skin, e.g., in a skin explant or cultured skin cells. In one embodiment, the method includes determining, e.g., in vitro or in vivo, whether a skin cell expresses corin. In another embodiment, the method includes evaluating the relative level of corin expression in a skin cell compared to a reference value, e.g., corin expression in a negative or positive DP cell control.

In one embodiment, corin expression in a skin cell is evaluated using a corin-binding agent, e.g., an anti-corin antibody, e.g., a polyclonal antibody; a monoclonal antibody or antigen binding fragment thereof; a modified antibody such as a chimeric antibody, reshaped antibody, humanized antibody, or fragment thereof (e.g., Fab', Fab, F(ab')$_2$); or a biosynthetic antibody, e.g., a single chain antibody, single domain antibody (DAB), Fv, single chain Fv (scFv), or the like. The antibody can be tagged with, e.g., a fluorescent tag (e.g., GFP), a radioactive tag, a myc tag, or a his tag. The antibody can be used to measure corin protein levels, e.g., by performing immunoprecipitation, immunohistochemistry, or western blot.

In another embodiment, corin expression is evaluated by evaluating the level or turnover of corin mRNA (e.g., performing hybridization assays such as in situ hybridization or northern blot).

In another embodiment, a corin biological activity is evaluated, e.g., a pro-ANP assay testing the ability of corin to process pro-ANP or related substrate, can be used to identify corin activity (see, e.g., Wu et al. (2002) J. Biol. Chem. 277:16900-16905).

In one embodiment, the DP cell is isolated following its identification. Isolated DP cells can be expanded in culture, e.g., under conditions that maintain the hair inductive capacity of the DP cells. It is not necessary that the cells continue to express corin. For example, the cells can be maintained under conditions in which they maintain their competence to express corin (although they may not in fact express corin). Corin expression can be re-established by contact to keratinocytes or materials therefrom (e.g., medium conditioned by keratinocytes, membranes derived from keratinocytes, or an extract from keratinocytes), e.g., in vitro or in a subject.

In another aspect, this disclosure features a method of identifying, e.g., labeling or tagging, a DP cell. The method includes evaluating a skin cell (e.g., one cell or a population of skin cells) for corin (e.g., a corin protein or nucleic acid). The evaluating can include determining if the cell can or is expressing corin (e.g., using a reporter gene). For example, the method includes contacting a skin cell with a corin binding agent, and evaluating for the presence or level of corin (e.g. coring protein or nucleic acid). The presence of corin identifies a cell as a DP cell. The corin binding agent can be, e.g., a nucleic acid, a polypeptide, e.g., an antibody described herein, a peptide fragment, a peptidomimetic, or a small molecule. An exemplary binding agent is an anti-corin antibody, e.g., an antibody described herein. The method is useful, e.g., for isolating DP cells or monitoring corin levels or DP cells (e.g., in DP cell culture).

DP cells can be expanded in culture, e.g., under conditions that maintain the hair inductive capacity of the DP cells and/or competence to express corin. Cell expansion can include growth and/or proliferation, e.g., one, two, three, four, five, or more cycles of cell division. In some embodiments, corin-expressing cells are selected from a population of expanded cells in culture, e.g., after co-culturing with a corin-inducing cell, e.g., a keratinocyte. The selection can be used to re-select corin-expressing cells from expanded cells in a population derived form an initial selection.

DP cells can be administered to a subject. In a preferred embodiment, the subject has an insufficient amount of hair or an insufficient rate of hair growth. In a preferred embodiment, the subject suffers from genetic pattern baldness; suffers from a hormonal disorder which decreases hair growth; has received a treatment, e.g., radiation, or chemotherapy, or a drug which inhibits hair growth; or has had a surgical procedure, e.g., skin graft, which is in need of hair growth.

The administered cell can be an autologous, allogeneic, or xenogeneic cell, but is preferably autologous. The autologous cell is preferably from a subject characterized with hair loss. For example, hair growth is promoted on: the subject's scalp; the subject's face, e.g., beard and/or mustache facial hair growth is promoted.

The administered cell can be inserted into hair follicles (e.g., existing or new hair follicles) or can administered as a component of new skin, e.g. a graft of artificial skin.

In another aspect, this disclosure features a method of isolating a corin-expressing cell. The method includes providing a corin binding agent, e.g., a corin antibody, contacting cells with the binding agent, and isolating a cell that expresses corin. The method can be used to isolate a skin cell, e.g., a DP cell, e.g., a mammalian DP cell, e.g., a human DP cell, e.g., a human scalp DP cell. In one embodiment, the starting population of cells is substantially free of cardiac cells, particularly cardiomyocytes. For example, the starting population of cells includes skin cells such as a population of cells derived from skin.

In one embodiment, the binding agent is an anti-corin antibody (e.g., an anti-corin antibody described herein) that is tagged with, e.g., a fluorescent tag (e.g., GFP), a radioactive tag, a magnetic tag, a myc tag, or a his tag. Skin cells to which the binding agent binds, e.g., DP cells, can be isolated via the binding agent tag, using, e.g., fluorescence activated cell sorting (FACS), magnetic activated cell sorting (MACS), chromatography, or column chromatography. In one embodiment, an anti-corin binding agent (e.g., an anti-corin antibody described herein) is directly or indirectly associated with (e.g., conjugated to) an insoluble substrate, e.g., a bead, e.g., a magnetic bead, and the cells are isolated using, e.g., gravity, centrifugation or immunomagnetic separation. The anti-corin binding agent can be associated with the insoluble support, before, during, or after contact to the skin cells.

Isolated cells can be expanded in culture, e.g., under conditions that maintain the hair inductive capacity of the DP cells and/or competence to express corin. In one embodiment, the cells are contacted with keratinocytes. Cells that are competent to express corin can be implanted into a subject, e.g., into follicles of a subject or as a skin graft, e.g., in combination with other epidermal cells, such as keratinocytes.

In another aspect, the disclosure features a population of corin-expression competent skin cells. The cells are isolated by a method that includes separating at least one corin-expressing cell from a population of cells that comprises skin cells. The method can include other features described herein. The population can include at least $10, 10^2, 10^3, 10^4, 10^5, 10^6, 10^7$, or $10^8$ cells.

In another aspect, the disclosure features a population of mammalian cells comprising at least $10^2, 10^3, 10^4, 10^5, 10^6, 10^7$, or $10^8$ cells corin-expression competent skin cells. The corin-expression competent cells constitute at least 30, 60, 70, 80, 90, 95, 98, 99, or 100% of the cell population. The population can be in a culture vessel. For example, the corin-expression competent cells constitute at least 50, 60, 70, 80, 90, 95, 98, 99% of the cell population in the vessel.

Also featured is a therapeutic composition that includes one or more cells, e.g., a population of such corin-expression competent skin cells.

Cells from a population, such as a therapeutic composition, can be evaluated for corin expression, e.g., using a method described herein. The cells can be contacted to a corin-binding agent. The cells can also be contacted to a keratinocyte or allowed to communicate with a keratinocyte cell, e.g., prior to evaluating corin expression.

In another aspect, this disclosure features a method for increasing hair follicle formation in a subject. The method includes administering corin-expression competent skin cells to a subject. The method can include, e.g., prior to the administering, evaluating corin expression for a subset (e.g., an aliquot) of such cells. The administered cells can be corin-expressing cells or non-corin expressing cells. The cells can be implanted in follicles. The cells can be administered e.g., with non-corin expression competent skin cells, e.g., keratinocytes or other corin-expression inducing cells.

In another aspect, this disclosure features a method for identifying an agent that modulates (e.g., inhibits or promotes) hair growth. The method includes identifying an agent that modulates, e.g., increases or decreases (e.g., permanently or temporarily), the expression, activity or levels of corin, e.g., in a skin cell, e.g., a DP cell such a corin-expressing DP cell or a corin-non-expressing DP cell. The method can also include correlating the ability of an agent to modulate corin expression, levels or activity with the ability to modulate hair growth. The method can further include selecting an identified agent, e.g., an agent that modulates hair growth.

In one embodiment, the agent is identified by evaluating the ability of a test agent to interact with, e.g., to bind, corin. In another embodiment, the agent is identified by evaluating the effect of a test agent to interact with a corin regulatory region, e.g., a promoter, e.g., a corin promoter (see, e.g., Pan et al. (2002) J. Biol. Chem. 277:38390-38398). In another embodiment, the agent is identified by evaluating the effect of a test agent on a DP cell culture or co-culture, e.g., a culture comprising a DP cell and a non-DP cell (e.g., a keratinocyte). In another embodiment, a pro-ANP assay testing the ability of corin to process pro-ANP can be used to identify corin agonists and antagonists (see, e.g., Wu et al. (2002) J. Biol. Chem. 277:16900-16905). In another embodiment, the agent is identified by evaluating, e.g., quantitatively or qualitatively evaluating, the ability of a test agent to modulate the hair growth of a corin transgenic animal, e.g., a corin transgenic animal described herein.

The test agent can be, e.g., a nucleic acid (e.g., an antisense, ribozyme), a polypeptide (e.g., an antibody or antigen-binding fragment thereof), a peptide fragment, a peptidomimetic, or a small molecule (e.g., a small organic molecule with a molecular weight of less than 2000 daltons). In another embodiment, the test agent is a member of a combinatorial library, e.g., a peptide or organic combinatorial library, or a natural product library. In one embodiment, a plurality of test agents, e.g., library members, is tested. For example, the test agents of the plurality, e.g., library, share structural or functional characteristics. The test agent can also be a crude or semi-purified extract, e.g., a botanical extract such as a plant extract or algal extract.

The method can include correlating the effect of the agent on corin expression, levels, or activity, with a predicted effect of the agent on a mammal, e.g., a human, e.g., by providing (e.g., to the government, a health care provider, insurance company or patient) informational, marketing or instructional material, e.g., print material or computer readable material (e.g., a label, an email), related to the agent or its use, identifying the effect of the agent as a possible or predicted effect of the agent in a mammal, e.g., a human. The method can include identifying the agent as a hair growth-modulating agent, e.g., in humans, if it increases corin expression, levels or activity, compared to a reference. The identification can be in the form of informational, marketing or instructional material, e.g., as described herein. In one embodiment, the method includes correlating a value for the evaluated parameter with altered hair growth or probability of altered hair growth, e.g., generating a dataset correlating a value for the evaluated parameter with altered hair growth or probability of altered hair growth.

In one embodiment, the method includes two evaluating steps, e.g., the method includes a first step of evaluating the test agent in a first system, e.g., a cell-free, cell-based, tissue system or animal model, and a second step of evaluating the test agent in a second system, e.g., a second cell or tissue system or in a non-human animal. In one embodiment, one of the evaluating steps includes evaluating the effect of the agent on a subject's skin or skin explant, e.g., evaluating the presence, extent or type of hair growth in the skin. The subject can be an experimental animal or a human. In one embodiment, the first evaluation includes testing the effect of the test agent on a corin promoter that is linked to a heterologous sequence such as a reporter polypeptide, and the second evaluation includes administering the test agent to a system, e.g., a cell based or animal system and evaluating effect of the agent on hair growth. In some embodiments, the method includes two evaluating steps in the same type of system, e.g., the agent is re-evaluated in a non-human animal after a first evaluation in the same or a different non-human animal. The two evaluations can be separated by any length of time, e.g., days, weeks, months or years.

In another embodiment, the identifying step includes: (a) providing an agent to a cell, tissue or non-human animal whose genome includes an exogenous nucleic acid that includes a regulatory region of a corin gene, e.g., a corin promoter (see, e.g., Pan et al. (2002) J. Biol. Chem. 277: 38390-38398), operably linked to a heterologous sequence, e.g., a nucleotide sequence encoding a reporter polypeptide (e.g., a colorimetric (e.g., LacZ) or fluorescently detectable reporter polypeptide, e.g. GFP, EGFP, BFP, RFP); (b) evaluating the ability of a test agent to modulate the expression of the reporter polypeptide in the cell, tissue or non-human animal; and (c) selecting a test agent that modulates the expression of the reporter polypeptide as an agent that modulates hair growth (e.g., modulates corin).

In one embodiment, the animal is an experimental animal. The animal can be wild type or a transgenic experimental animal, e.g., a corin transgenic rodent, e.g., a corin transgenic mouse described herein, e.g., an animal with altered corin expression or a reporter for detecting competence to express corin. The subject can also be a human. In one embodiment, the evaluating step comprises administering the agent to the subject and evaluating hair growth. In another embodiment, the cell or tissue is a skin cell, e.g., a mesenchymal cell, e.g., a DP cell; or tissue, e.g., a skin explant. In yet another embodiment, a cell, e.g., a skin cell, e.g., a DP cell, or a tissue, e.g., a skin explant, is derived from a transgenic animal.

In another aspect, this disclosure features an isolated skin cell containing an exogenous nucleic acid that includes a nucleotide sequence encoding a reporter polypeptide (e.g., a colorimetric (e.g., LacZ) or fluorescently detectable reporter polypeptide, e.g. GFP, EGFP, BFP, RFP) operably linked to a corin gene promoter or a portion thereof (see, e.g., Pan et al. (2002) J. Biol. Chem. 277:38390-38398), e.g., −405 to −15 in the human corin gene, or −900 to −15, −900 to +60, −700 to +60, or −500 to +60. The skin cell can be, e.g., a mammalian skin cell, e.g., a human or mouse skin cell. In one embodiment, the skin cell is a DP cell.

In another aspect, this disclosure features a transgenic non-human animal having a corin transgene expressed specifically in the skin. Some embodiments feature a transgenic cell, e.g., a DP cell; tissue, e.g., skin or hair follicle; or non-human mammal, e.g., a rodent, e.g., a mouse, rat, guinea pig, or rabbit, containing a corin transgene that is operably linked to a promoter sequence sufficient to direct corin expression in a skin cell, e.g., a DP cell or other hair follicle cell. The transgenic cell, e.g., a transgenic DP cell, can modulate hair growth. Transgenic tissue or a transgenic animal can have altered hair growth. The corin transgene may be contained in the germ and/or somatic cells; alternatively, the corin transgene may be contained only in a certain type of cell, e.g., a DP cell.

Another aspect of this disclosure features an isolated nucleic acid sequence encoding a corin polypeptide, or a functional fragment or variant thereof, operably linked to an expression control sequence, e.g., a corin promoter, sufficient to drive expression of corin in a specific cell type, e.g., a skin cell, e.g., a DP cell. The nucleic acid may be an integral part of a linear construct or of a vector, e.g., a plasmid, e.g., an expression plasmid or a replicating plasmid, or a viral vector, e.g. lambda-ZAP. The vector may be harbored in a host, e.g., E. coli or bacteriophage. Also included are host cells, e.g., mammalian host cells, e.g., skin cells, that include the nucleic acid and/or vectors described herein. In one embodiment, the skin cell (e.g., DP cell) includes a nucleic acid encoding an amino acid sequence variant of corin, e.g., a dominant negative or a hyperactive corin variant.

In another aspect, this disclosure features a method of treating a subject. The method includes (a) identifying a subject, e.g., a subject desirous, or in need, of altered hair growth; and (b) administering to the subject an agent that modulates corin in the subject, e.g., administering to the subject an effective amount of an agent that increases or decreases the activity, level or expression of corin, e.g., an agent described herein. Preferably, the agent is administered to the subject's skin, e.g., topically.

In one embodiment, the agent is administered via a liposome carrier, e.g., a lecithin liposome or an alkylphospholipid liposome. The agent can be administered to the face, chest, neck, hands, and other regions of the body. The treatment can involve more than one administration, e.g., at least two, three, or four administrations, of the agent. The treatment can also involve daily administration of the agent.

In one embodiment, the method includes administering the agent in combination with a second treatment, e.g., a second treatment for hair growth, e.g., minoxidil (available from the Upjohn Co. of Kalamazoo, Mich.), cyclosporin, and natural or synthetic steroid hormones and their enhancers and antagonists, e.g., anti-androgens.

In some embodiments, the method includes evaluating the subject for hair growth. The evaluation can be performed before, during, and/or after the administration of the agent. For example, the evaluation can be performed at least 1 day, 2 days, 4, 7, 14, 21, 30 or more days before and/or after the administration.

In another embodiment, the administration of an agent can be initiated: when the subject begins to show signs of a hair growth-related disorder; when a hair growth-related disorder, e.g., alopecia, is diagnosed; at the time a treatment for a hair growth-related disorder is begun or begins to exert its effects; or generally, as is needed to modulate hair growth.

The period over which the agent is administered, or the period over which clinically effective levels are maintained in the subject, can be long term, e.g., for six months or more or a year or more, or short term, e.g., for less than a year, six months, one month, two weeks or less.

The identification of a subject in need of altered hair growth can be performed e.g., by the subject, by a health care provider, by a provider of a hair growth treatment, by a provider of a hair removal treatment, or another party. The agent may be administered, e.g., by the subject, by a health care provider, by a provider of a hair growth treatment, by a provider of a hair removal treatment, or another party. Likewise, the evaluation of the effect on hair growth may be performed, e.g., by the subject, by a health care provider, by a provider of a hair growth treatment, by a provider of a hair removal treatment or another party. Suitable subjects include, e.g., subjects who have or are at risk for hair loss.

An agent that increases corin to thereby increase hair growth can be, for example: a corin polypeptide, or a functional fragment or variant thereof; a peptide or protein agonist or antagonist of a corin that modulates corin expression, levels or activity; a small molecule that modulates expression of corin, e.g., by binding to the promoter region of its gene; a chemical compound, e.g., an organic compound, e.g., a naturally occurring or synthetic organic compound that modulates expression of corin; a nucleotide sequence encoding a corin polypeptide, or a fragment or analog thereof; an antibody, e.g., an antibody that binds to and stabilizes or assists the binding of corin to a binding partner; or a crude or semi-purified extract, e.g., a botanical extract such as a plant extract or algal extract. The nucleotide sequence can be a genomic sequence or a cDNA sequence. The nucleotide sequence can include: a corin coding region; a promoter sequence, e.g., a promoter sequence from a corin gene or from another gene; an enhancer sequence; untranslated regulatory sequences, e.g., a 5' untranslated region (UTR), e.g., a 5' UTR from a corin gene or from another gene, a 3' UTR, e.g., a 3' UTR from a corin gene or from another gene; a polyadenylation site; or an insulator sequence. In another embodiment, the level of corin is increased by increasing the level of expression of endogenous corin, e.g., by increasing transcription of the corin gene or increasing corin mRNA stability. In yet another embodiment, transcription of the corin gene is increased by: altering the regulatory sequence of the endogenous corin gene, e.g., in a somatic cell, e.g., by the addition of a positive regulatory element, such as an enhancer or a DNA-binding site for a transcriptional activator; the deletion of a negative regulatory element, such as a DNA-binding site for a transcriptional repressor; and/or replacement of the endogenous regulatory sequence, or elements therein, with that of another gene, thereby allowing the coding region of the corin gene to be transcribed more efficiently.

An agent that decreases corin to thereby decrease hair growth can be, for example: a corin binding protein, e.g., a soluble corin binding protein that binds and inhibits a corin activity, or inhibits the ability of corin to interact with a binding partner; an antibody that specifically binds to the corin protein, e.g., an antibody that disrupts the ability of corin to bind to a binding partner; a mutated inactive corin or fragment thereof that binds to corin but disrupts a corin activity; a corin nucleic acid molecule that can bind to a cellular corin nucleic acid sequence, e.g., mRNA, and can inhibit expression of the protein, e.g., an antisense, siRNA molecule or corin ribozyme; an agent that decreases corin gene expression, e.g., a small molecule that binds the promoter of corin; or a crude or semi-purified extract, e.g., a botanical extract such as a plant extract or algal extract. In another embodiment, corin is inhibited by decreasing the level of expression of an endogenous corin gene, e.g., by decreasing transcription of the corin gene. In yet another embodiment, transcription of the corin gene can be decreased by: altering the regulatory sequences of the endogenous corin gene, e.g., by the addition of a negative regulatory sequence, such as a DNA-binding site for a transcriptional repressor, or by the removal of a positive regulatory sequence, such as an enhancer or a DNA-binding site for a transcriptional activator. In another embodiment, the antibody that binds corin is a monoclonal antibody, e.g., a humanized chimeric or human monoclonal antibody.

In another aspect, this disclosure features compositions containing an agent, e.g., an agent described herein, e.g., an agent identified by a screening method described herein, that modulates the expression, activity, or level of corin, for modulating hair growth. In another embodiment, the composition is a cosmetic composition, e.g., formulated for topical administration. The composition is effective to modulate hair growth when applied to the skin, e.g., for a period of at least 1 day, e.g., at least 7 days, e.g., 14, 30, 60, 90 days, or it can be effective to modulate hair growth for a longer term, e.g., at least 6 to 9 months or longer. In one embodiment, the composition also has a fragrance, a preservative, or other cosmetic ingredient, e.g., a moisturizer, or sunscreen agent, e.g., octyl methoxycinnamate, aminobenzoic acid, oxybenzone, padimate O, homosalate, or titanium dioxide. The composition can be provided in a shampoo, oil, cream, lotion, soap, foam, gel, or other cosmetic preparation. In another embodiment, the composition also has a cosmetic ingredient, e.g., a fragrance or moisturizer.

In another aspect, this disclosure features a method of modulating hair growth in a subject. The method includes supplying to the subject a composition containing an agent that affects the expression, activity or level of a component of corin, e.g., an agent described herein, e.g., an agent identified by a screening method described herein, and supplying to the subject application instructions for hair growth.

In another aspect, this disclosure features a kit for modulating hair growth of a subject that includes a composition described herein, e.g., a composition containing an agent that affects the expression, activity, or level of a component of corin; and instructions for use, e.g., instructions to apply the composition to an area of the body in need of hair growth. In a preferred embodiment, the composition also has a cosmetic ingredient, e.g., a fragrance or moisturizer.

An effective amount of the agent of the present invention is defined as the amount of a composition that, upon administration to a subject, modulates hair growth in the subject. The effective amount to be administered to a subject is typically based on a variety of factors including age, sex, surface area, weight, and conditions of the skin. Body surface area may be approximately determined from height and weight of the patient. See, e.g., Scientific Tables, Geigy Pharmaceuticals, Ardley, N.Y., 1970, 537. Effective doses will vary, as recognized by those skilled in the art, dependent on route of administration, excipient usage, and the possibility of co-usage with other treatments such as usage of other hair growth-modulating compounds.

In another aspect, this disclosure provides a method of determining if a subject is at risk for or has a hair growth-related disorder, e.g., alopecia. The method includes: (a) evaluating the level, activity, expression and/or genotype of corin in a subject, e.g., in a biological sample of the subject, and (b) correlating an alteration in corin, e.g., a non-wild-type level, activity, expression, and/or genotype of corin, with a risk for or presence of a hair growth-related disorder, e.g., alopecia. Correlating can include identifying the alteration as a risk or diagnostic factor of a hair growth-related disorder, e.g., providing a print material or computer readable medium, e.g., an informational, diagnostic, marketing or instructional print material or computer readable medium, to, e.g., the subject or to a health care provider, identifying the alteration as a risk or diagnostic factor for a hair growth-related disorder.

In one embodiment, the method includes diagnosing a subject as being at risk for or having a hair growth-related disorder, e.g., alopecia. In another embodiment, the method includes prescribing or beginning a treatment for a hair growth-related disorder, e.g., alopecia, in the subject. In some embodiments, the method includes performing a second diagnostic test for a hair growth-related disorder, e.g., alopecia. The second diagnostic test can include, e.g., repeating the evaluation of the level, activity, expression and/or genotype of corin in the subject.

The subject can be a human, e.g., a human with a family history of a hair growth-related disorder, e.g., alopecia. The biological sample can be a cell sample, tissue sample, or at least partially isolated molecules, e.g., nucleic acids, e.g., genomic DNA, cDNA, mRNA, and/or proteins derived from the subject. Such methods are useful, e.g., for diagnosis of a hair growth-related disorder, e.g., alopecia, or risk for a hair growth-related disorder, e.g., alopecia.

In a one embodiment, the method includes one or more of the following:
1) detecting, in a biological sample of the subject, the presence or absence of a mutation that affects the expression of corin, or detecting the presence or absence of a mutation in a region which controls the expression of the gene, e.g., a mutation in the 5' control region, the presence of a mutation being indicative of risk;
2) detecting, in a biological sample of the subject, the presence or absence of a mutation that alters the structure of corin, the presence of a mutation being indicative of risk;

3) detecting, in a biological sample of the subject, the misexpression of corin, at the mRNA level, e.g., detecting a non-wild-type level of a corin mRNA, non-wild-type levels of corin mRNA being associated with risk. Detecting misexpression can include ascertaining the existence of at least one of: an alteration in the level of a mRNA transcript of corin compared to a reference, e.g., as compared to a baseline value or to levels in a subject not at risk for a hair growth-related disorder; the presence of a non-wild-type splicing pattern of a mRNA transcript of the gene; or a non-wild-type level of corin protein e.g., as compared to a reference, e.g., compared to a baseline value, or to levels in a subject not at risk for a hair growth-related disorder;

4) detecting, in a biological sample of the subject, the misexpression of corin, at the protein level, e.g., detecting a non-wild-type level of a corin polypeptide, decreased or increased levels of corin protein (e.g., compared to a control) being indicative of a risk. For example, the method can include contacting a sample from the subject with an antibody to corin protein;

5) detecting, in a biological sample of the subject, a polymorphism, e.g., a SNP, in the corin gene, which is associated with a hair growth-related disorder. In another embodiment the method includes: ascertaining the existence of at least one of: an insertion or a deletion of one or more nucleotides from the corin gene; a point mutation, e.g., a substitution of one or more nucleotides of the gene; a gross chromosomal rearrangement of the gene, e.g., a translocation, inversion, duplication or deletion. In yet another embodiment, a SNP or haplotype associated with hair growth-related disorder risk is detected.

In one embodiment, detecting a mutation or polymorphism can include: (i) providing a probe or primer, e.g., a labeled probe or primer, that includes a region of nucleotide sequence which hybridizes to a sense or antisense sequence from the corin gene, or naturally occurring mutants thereof, or to the 5' or 3' flanking sequences naturally associated with the corin gene; (ii) exposing the probe/primer to nucleic acid of the subject; and (iii) detecting, e.g., by hybridization, e.g., in situ hybridization to the nucleic acid; or amplification of the nucleic acid, the presence or absence of the mutation or polymorphism.

In another aspect, this disclosure features a computer readable record encoded with (a) a subject identifier, e.g., a patient identifier, (b) one or more results from an evaluation of the subject, e.g., a diagnostic evaluation described herein, e.g., the level of expression, level or activity of corin in the subject, and optionally (c) a value for or related to a disorder or condition state, e.g., a value correlated with disorder status or risk with regard to a hair growth-related disorder, e.g., alopecia. In one embodiment, the disclosure features a computer medium having a plurality of digitally encoded data records. Each data record includes a value representing the level of expression, level or activity of corin in a sample, and a descriptor of the sample. The descriptor of the sample can be an identifier of the sample; a subject from which the sample was derived, e.g., a patient; a diagnosis; or a treatment, e.g., a treatment described herein. In one embodiment, the data record further includes values representing the level of expression, level or activity of genes other than corin, e.g., other genes associated with hair growth or other genes on an array. The data record can be structured as a table, e.g., a table that is part of a database such as a relational database, e.g., a SQL database of the Oracle or Sybase database environments. The disclosure also includes a method of communicating information about a subject, e.g., by transmitting information, e.g., transmitting a computer readable record described herein, e.g., over a computer network.

In another aspect, this disclosure features a method of providing information, e.g., for making a decision with regard to the treatment of a subject having, or at risk for, a disorder described herein. The method includes (a) evaluating the expression, level or activity of corin; optionally (b) providing a value for the expression, level or activity of corin; optionally (c) comparing the provided value with a reference value, e.g., a control or non-disorder state reference or a disorder state reference; and optionally (d) based, e.g., on the relationship of the provided value to the reference value, supplying information, e.g., information for making a decision on or related to the treatment of the subject.

In one embodiment, the provided value relates to an activity described herein, e.g., to corin activity described herein.

In one embodiment, the decision is whether to administer a preselected treatment.

In another embodiment, the decision is whether a party, e.g., an insurance company, a health maintenance organization (HMO), or other entity, will pay for all or part of a preselected treatment.

Also featured is a method of evaluating a sample. The method includes providing a sample, e.g., from the subject, and determining a gene expression profile of the sample, wherein the profile includes a value representing the level of expression of corin. The method can further include comparing the value or the profile (i.e., multiple values) to a reference value or reference profile. The gene expression profile of the sample can be obtained by methods known in the art, e.g., by providing a nucleic acid from the sample and contacting the nucleic acid to an array. The method can be used to diagnose a hair growth-related condition, e.g., decreased or non-optimal hair growth, e.g., alopecia, in a subject wherein misexpression of corin, e.g., an decrease in expression of corin, is an indication that the subject has or is disposed to having hair loss, e.g., alopecia. The method can be used to monitor a treatment in a subject. For example, the gene expression profile can be determined for a sample from a subject undergoing treatment. The profile can be compared to a reference profile or to a profile obtained from the subject prior to treatment or prior to onset of the disorder (see, e.g., Golub et al. (1999) Science 286:531).

As used herein, the term "DP cell" or "dermal papilla cell" refers a DP cell as found in a subject, or a cell from skin that expresses corin or has competence to express corin, e.g., when present in an appropriate milieu. A DP cell can also be able to induce hair follicle formation and/or growth. DP cells isolated from skin can reduce or stop expressing corin, but remain competent to express corin, e.g., when present in an appropriate milieu. For example, corin expression can be restored by contact to keratinocytes (including direct contact to keratinocyte cells or materials from such cells, e.g., inductive signals between such cells and the DP cells).

As used herein, the term "corin-expression competent cell" refers to a cell that may or may not express corin, but which can express corin when in an appropriate milieu, e.g., when in contact with keratinocytes or materials from such cells, e.g., inductive signals from keratinocytes. In one exemplary method, corin-competence for skin cells can be evaluated by co-culturing such cells with keratinocytes.

Hair restoration methods represent a large market. Conventional approaches to hair restoration therapy entail the implantation of intact follicles harvested from elsewhere on the body to thinning regions of the scalp. Hair follicle transplants are limited by the number of follicles available for grafting and the expense associated with manual implantation of individual hair plugs.

DP cells in vivo can stimulate hair growth in intact follicles, and DP cell grafts can induce the formation of hair follicles. To routinely use DP cells for implants and other processes, it would be useful to have methods for procuring substantial numbers of DP cells or related cells that have hair-inductive properties.

Known techniques for isolating DP cells from the DP organ include explanting a DP from a hair follicle, culturing the explant, and allowing the DP cells to emigrate from the DP explant into the culture (see, e.g., Messenger (1984) British J. of Dermatol. 110:685-689; Magerl et al. (2002) Exp. Dermatol. 11:381-385). Alternatively, DP cells can be manually dissected from a DP. These techniques are adequate for the isolation of small numbers of DP cells. Such cells can be expanded, e.g., by the methods described herein, and, for example, evaluated, e.g., for corin expression.

The methods described herein provide means to isolate large numbers of DP cells, e.g., for clinical applications, including implanting DP cells obtained from the same or a different subject into a subject, e.g., to increase hair formation. The implanted cell can be an autologous, allogeneic, or xenogeneic cell, but is preferably autologous. The autologous cell is preferably from a subject characterized with hair loss. For example, hair growth is promoted on: the subject's scalp; the subject's face, e.g., beard and/or mustache facial hair growth is promoted.

In a preferred embodiment, the subject has an insufficient amount of hair or an insufficient rate of hair growth. In a preferred embodiment, the subject suffers from genetic pattern baldness; suffers from a hormonal disorder which decreases hair growth; has received a treatment, e.g., radiation, or chemotherapy, or a drug which inhibits hair growth; or has had a surgical procedure, e.g., skin graft, which is in need of hair growth.

The details of one or more embodiments are set forth in the accompanying drawings and the description below. Other features, objects, and advantages will be apparent from the description and drawings, and from the claims.

DETAILED DESCRIPTION

Corin Protein

Figure 1:
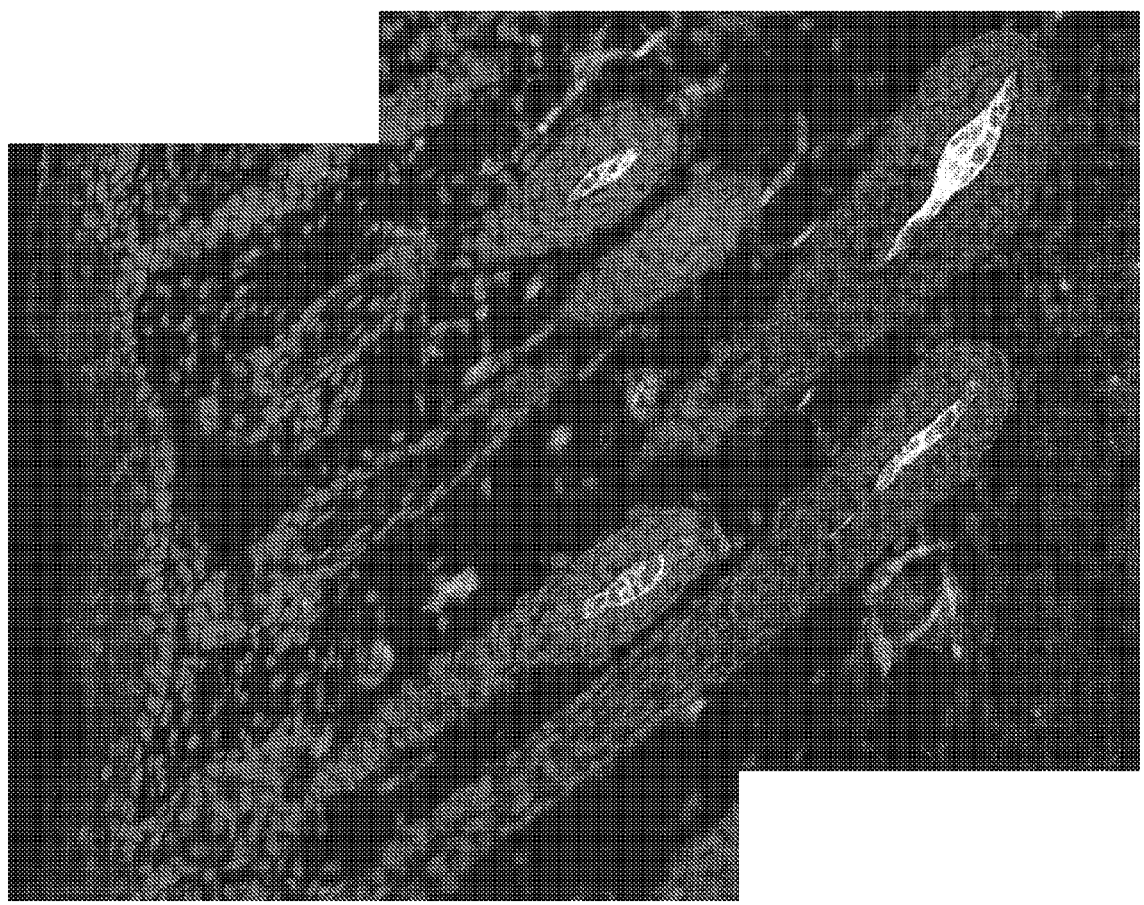
FIG. 1 is a micrograph of mouse skin stained with anti-LRP4 antibody.

Corin is a type II transmembrane protein with an extracellular domain that includes protease, LDL receptor, frizzled, and scavenger receptor domains. The human corin gene is expressed in cardiac myocytes and corin protein can cleave proAtrial Natriuretic Peptide (proANP), a hormone involved in regulating blood pressure, has been reported (Yan (1999) J. Biol. Chem. 274:14926-14935; Yan et al. (2000) Proc. Natl. Acad. Sci. USA 97:8525-8529; Pan et al. (2002) J. Biol. Chem. 277:38390-38398; Wu et al. (2002) J. Biol. Chem. 277:16900-16905). Murine corin (LRP4) is shown to be expressed in the heart (Tomita et al. (1998) J. Biochem. 124: 784-789).

The inventors have discovered, inter alia, the corin is also expressed in specialized cells of non-cardiac tissue, e.g., in specialized cells of the skin. Accordingly, corin expression can be used to evaluate and characterized the distribution of specialized cells in non-cardiac tissue and to isolated such cells or to identify agents that modulate the function of such cells. For example, corin expression can be used as a marker to isolated dermal papilla cells from skin.

An exemplary human corin amino acid sequence is as follows (SEQ ID NO:1; Yan et al. (1999) J. Biol. Chem. 274:14926-14935):

```
MKQSPALAPE ERYRRAGSPK PVLRADDNNM GNGCSQKLAT ANLLRFLLLV

LIPCICALVL LLVILLSYVG TLQKVYFKSN GSEPLVTDGE IQGSDVILTN

TIYNQSTVVS TAHPDQHVPA WTTDASLPGD QSHRNTSACM NITHSQCQML

PYHATLTPLL SVVRNMEMEK FLKFFTYLHR LSCYQHIMLF GCTLAFPECI

IDGDDSHGLL PCRSFCEAAK EGCESVLGMV NYSWPDFLRC SQFRNQTESS

NVSRICFSPQ QENGKQLLCG RGENFLCASG ICIPGKLQCN GYNDCDDWSD

EAHCNCSENL FHCHTGKCLN YSLVCDGYDD CGDLSDEQNC DCNPTTEHRC

GDGRCIAMEW VCDGDHDCVD KSDEVNCSCH SQGLVECRNG QCIPSTFQCD

GDEDCKDGSD EENCSVIQTS CQEGDQRCLY NPCLDSCGGS SLCDPNNSLN

NCSQCEPITL ELCMNLPYNS TSYPNYFGHR TQKEASISWE SSLFPALVQT

NCYKYLMFFS CTILVPKCDV NTGERIPPCR ALCEHSKERC ESVLGIVGLQ

WPEDTDCSQF PEENSDNQTC LMPDEYVEEC SPSHFKCRSG QCVLASRRCD

GQADCDDDSD EENCGCKERD LWECPSNKQC LKHTVICDGF PDCPDYMDEK

NCSFCQDDEL ECANHACVSR DLWCDGEADC SDSSDEWDCV TLSINVNSSS

FLMVHRAATE HHVCADGWQE ILSQLACKQM GLGEPSVTKL IQEQEKEPRW
```

```
                             -continued
LTLHSNWESL  NGTTLHELLV  NGQSCESRSK  ISLLCTKQDC  GRRPAARMNK

RILGGRTSRP  GRWPWQCSLQ  SEPSGHICGC  VLIAKKWVLT  VAHCFEGREN

AAVWKVVLGI  NNLDHPSVFM  QTRFVKTIIL  HPRYSRAVVD  YDISIVELSE

DISETGYVRP  VCLPNPEQWL  EPDTYCYITG  WGHMGNKMPF  KLQEGEVRII

SLEHCQSYFD  MKTITTRMIC  AGYESGTVDS  CMGDSGGPLV  CEKPGGRWTL

FGLTSWGSVC  FSKVLGPGVY  SNVSYFVEWI  KRQIYIQTFL  LN
```

Corin includes a number of different domains. At its N terminus, corin has a cytoplasmic domain and an integral transmembrane domain. This is followed by an extracellular region that includes two frizzled-like cysteine-rich motifs, eight low density lipoprotein receptor repeats, a macrophage scavenger receptor-like domain, and a trypsin-like protease domain at the C terminus (Yan et al. (1999) J. Biol. Chem. 274:14926-14935; Hooper et al. (2000) Eur. J. Biochem. 267:6931-6937). A corin may be glycosylated at one or more amino acid residues. The overall topology of corin is similar to those of other type II transmembrane serine proteases of the trypsin superfamily (Hooper et al. (2001) J. Biol. Chem. 276:857-860), such as hepsin (Leytus et al. (1988) Biochem. 27:1067-1074; Wu (2001) Front. Biosci. 6:D192-D200) and enterokinase (Kitamoto (1994) Proc. Natl. Acad. Sci. USA 91:7588-7592).

TABLE 1

Corin Features (referring to SEQ ID NO: 1)

| Key | From | To | Length | Description |
|---|---|---|---|---|
| DOMAIN | 1 | 45 | 45 | Cytoplasmic |
| TRANSMEM | 46 | 66 | 21 | Signal-anchor for type II membrane protein |
| DOMAIN | 67 | 1042 | 976 | Extracellular |
| DOMAIN | 134 | 259 | 126 | FZ 1. |

TABLE 1-continued

Corin Features (referring to SEQ ID NO: 1)

| Key | From | To | Length | Description |
|---|---|---|---|---|
| DOMAIN | 268 | 304 | 37 | LDL-receptor class A 1. |
| DOMAIN | 305 | 340 | 36 | LDL-receptor class A 2. |
| DOMAIN | 341 | 377 | 37 | LDL-receptor class A 3. |
| DOMAIN | 378 | 415 | 38 | LDL-receptor class A 4. |
| DOMAIN | 450 | 573 | 124 | FZ 2. |
| DOMAIN | 579 | 614 | 36 | LDL-receptor class A 5. |
| DOMAIN | 615 | 653 | 39 | LDL-receptor class A 6. |
| DOMAIN | 654 | 690 | 37 | LDL-receptor class A 7. |
| DOMAIN | 690 | 786 | 97 | SRCR. |
| DOMAIN | 802 | 1042 | 241 | Serine protease. |
| ACT_SITE | 843 | 843 | | Charge relay system |
| ACT_SITE | 892 | 892 | | Charge relay system |
| ACT_SITE | 985 | 985 | | Charge relay system. |
| DISULFID | 790 | 912 | | |
| DISULFID | 828 | 844 | | |
| DISULFID | 955 | 970 | | |
| DISULFID | 981 | 1010 | | |

The gene encoding human corin is located at in genomic location: 47436946-47680987 bp or 47436846:47681987 (47.4 Mb) on chromosome 4. This gene is located in sequence: AC107068.3.1.181804. An exemplary portion of this region, which can include regulatory sequences, includes (include an untranslated region and first exon in bold):

```
                                                    (SEQ ID NO:2)
TACATTTGATCTCACTTCAGAAACAAAATACTGCCCCCCCCATTTTACAAATGCATATT

TTTTTCTCAGCAATAATGTTCAAGAACAAGTGCTTGGCCCATATTTTGTTGTCTTTACA

TGGCTTTCTTTAAATAATGGGGATGGATTTATTAAATAACCTCATGAGTAATTTTCAAA

ATTTCCATTAAGATCTTGATTGAAATTGGATGAAAAATCATTTCTAAGAAAAACCCAAT

GAAGTGTTTTCTTTGCCACATTTGACAATTGCCTTGGACTTGGTAAAGTAATCATTAC

TGTGTTGAGTACCTCCAGTGCCCTCCTTGACGCTGCCTTAGAAAAGGTAGCTGCTTTTG

AATGACAGGCAGGAATTTGTTCGCCTTTTAGGTTCAGCCTGTAGGTGCCCTCTGCAGGA

AATCAGGAACTAGGGTTTTGGAAGCAGTCAGGGTGGGGTTCTCCCTTGTCCCTGCAGCC

TCAGCAAAGACTCAGGCAGTCTGGCAAAAGCAGTTTCTTCAGCATACCTAACAGAACGC

AAGTTTCCATATGCCTGATGCAAATAATGGCCTCCAAACGTTAAACCTTTTTTGAGATA

AACTTGTTCTTTAATTGCCAGCGCCTGCAGTTAATTTTGATTGGCTACACTCTGGTTAA

AAGAAAATGCTTTCGATGTGATATGGCAAATTTGGAGAAAAGTAACTCTTTTGCTCCCA

ACCAGTCTTCCACAACTTAAACTTAATCGTCCTGTCCTTTTCTGCTGCCCTCGTGGAGT

GTAAGTTTTGAGGGAGACCAGCAGAAACTGACTTTCCATATGCCCCTGAAGAATAACT
```

-continued

```
TCTTTGAATGCAAAGAGGTGGGGACACGGAGGATCTGTCATTACGGGTTATTATGGGTG

GGACCCAGAGACGGGAGTGAAGGGAGGGTGTGGCCCGCGGGTGGGATCTGTAGAGCAGA

CAAAATATGGGGCCCCTGGCGCTTAAAGTTCAGTTTGTCTCTCTTGAGCTTGGAGAAAA

TCATCCGTAGTGCCTCCCCGGGGGACACGTAGAGGAGAGAAAAGCGACCAAGATAAAAG

TGGACAGAAGAATAAGCGAGACTTTTTATCCATGAAACAGTCTCCTGCCCTCGCTCCGG

AAGAGCGCTGCCGCAGAGCCGGGTCCCCAAAGCCGGTAAGATCGATGATTCGCTGTCCT

ACCGCAGCCAGGTGTGATGG
```

Identifying DP Cells

Corin is expressed in DP cells of the skin. DP cells can be identified using corin expression as a marker. A variety of methods can be used to detect corin expression. For example, corin protein or corin nucleic acid can be evaluated. Corin expression can be also be detected without evaluating corin protein or corin nucleic acid directly. For example, the cells may contain a reporter gene or other indicator of corin expression.

In one embodiment, the presence, level, or absence of corin in skin cells can be determined using, e.g., a corin binding agent, e.g., a corin-protein binding agent, particularly an agent that recognizes the extracellular region of the corin protein. Suitable corin binding agents can include, e.g., a nucleic acid, a polypeptide, e.g., an antibody, a peptide fragment, a peptidomimetic, or a small molecule.

An anti-corin antibody can be, e.g., a polyclonal antibody; a monoclonal antibody or antigen binding fragment thereof; a modified antibody such as a chimeric antibody, reshaped antibody, humanized antibody, or fragment thereof (e.g., Fab', Fab, F(ab')$_2$); or a biosynthetic antibody, e.g., a single chain antibody, single domain antibody (DAB), Fv, single chain Fv (scFv), or the like.

Methods of making and using polyclonal and monoclonal antibodies to detect a particular target are described, e.g., in Harlow et al., Using Antibodies: A Laboratory Manual: Portable Protocol I. Cold Spring Harbor Laboratory (Dec. 1, 1998). Methods for making modified antibodies and antibody fragments (e.g., chimeric antibodies, reshaped antibodies, humanized antibodies, or fragments thereof, e.g., Fab', Fab, F(ab')$_2$ fragments); or biosynthetic antibodies (e.g., single chain antibodies, single domain antibodies (DABs), Fv, single chain Fv (scFv), and the like), are known in the art and can be found, e.g., in Zola, *Monoclonal Antibodies: Preparation and Use of Monoclonal Antibodies and Engineered Antibody Derivatives*, Springer Verlag (Dec. 15, 2000; 1st edition).

In one embodiment, the corin-binding agent (such as an antibody) is associated with a detectable "label." The term "labeled," with regard to the probe or antibody, is intended to encompass direct labeling of the probe or antibody by coupling (e.g., physically linking) a detectable substance to the probe or antibody, as well as indirect labeling of the probe or antibody by reactivity with a detectable substance. The corin-binding agent can be labeled with, e.g., a fluorescent tag, e.g., GFP, a radioactive tag, a myc tag, or a his tag. The corin-binding agent can be associated with, e.g., directly or indirectly, to an insoluble support such as a bead, e.g., a magnetic bead. For example, the corin-binding agent can be coupled to the insoluble support.

The detection methods can be used to detect corin in a biological sample, e.g., skin, e.g., skin cells, in vitro as well as in vivo. In vitro techniques for detection include enzyme linked immunosorbent assays (ELISAs), immunoprecipitation, immunofluorescence, enzyme immunoassay (EIA), radioimmunoassay (RIA), and Western blot analysis. In vivo techniques for detection of corin include introducing into a subject a labeled corin-binding agent, e.g., an antibody. For example, the corin-binding agent can be labeled with a radioactive marker that allows the presence and location of the corin-binding agent in a subject to be detected by standard imaging techniques. In another embodiment, a sample obtained from the subject is labeled, e.g., biotinylated and then contacted to the corin-binding agent, e.g., an antibody positioned on an antibody array. The sample can be detected, e.g., with avidin coupled to a fluorescent label.

The presence, level, or absence of corin in skin cells can also be evaluated by contacting skin cells with a compound or an agent capable of detecting corin nucleic acid, e.g., mRNA or genomic DNA, that encodes corin such that the presence of the nucleic acid is detected. The level of mRNA corresponding to corin in a cell can be determined both by in situ and by in vitro methods.

Isolated mRNA can be used in hybridization or amplification assays that include, but are not limited to, Southern or Northern analyses, polymerase chain reaction analyses and probe arrays. An exemplary diagnostic method for the detection of mRNA levels includes contacting the isolated mRNA with a nucleic acid molecule (probe) that can hybridize to the mRNA encoded by the gene being detected. The nucleic acid probe can be, for example, a full-length nucleic acid, or a portion thereof, such as an oligonucleotide of at least 7, 15, 30, 50, 100, 250 or 500 nucleotides in length and sufficient to specifically hybridize under stringent conditions to mRNA, cDNA or genomic DNA encoding corin. Guidance for performing hybridization reactions can be found in *Current Protocols in Molecular Biology*, John Wiley & Sons, N.Y. (1989), 6.3.1-6.3.6. Aqueous and nonaqueous methods are described in that reference and either can be used. Examples of pecific hybridization conditions include: 1) low stringency hybridization conditions in 6× sodium chloride/sodium citrate (SSC) at about 45° C., followed by two washes in 0.2×SSC, 0.1% SDS at least at 50° C. (the temperature of the washes can be increased to 55° C. for low stringency conditions); 2) medium stringency hybridization conditions in 6×SSC at about 45° C., followed by one or more washes in 0.2×SSC, 0.1% SDS at 60° C.; 3) high stringency hybridization conditions in 6×SSC at about 45° C., followed by one or more washes in 0.2×SSC, 0.1% SDS at 65° C.; and preferably 4) very high stringency hybridization conditions are 0.5M sodium phosphate, 7% SDS at 65° C., followed by one or more washes at 0.2×SSC, 1% SDS at 65° C.

The probe can be disposed on an address of an array, e.g., an array described below. Other suitable probes for use in the diagnostic assays are described herein.

In one format, mRNA or cDNA is immobilized on a surface and contacted with the probes, for example by running the isolated mRNA on an agarose gel and transferring the mRNA from the gel to a membrane, such as nitrocellulose. In an alternative format, the probes are immobilized on a surface and the mRNA or cDNA is contacted with the probes, for example, in a two-dimensional gene chip array described below. A skilled artisan can adapt known mRNA detection methods for use in detecting the level of mRNA encoded by the gene. The level of mRNA in a sample that is encoded by a gene can be evaluated by nucleic acid amplification, e.g., by rtPCR.

For in situ methods, a cell, e.g., a skin cell, or tissue, e.g., skin, sample can be prepared/processed and immobilized on a support, typically a glass slide, and then contacted with a probe that can hybridize to mRNA that encodes the gene being analyzed.

In another embodiment, the methods further include contacting a control sample, e.g., cells not from the skin or the heart, e.g., cells from spleen, thymus, skeletal muscle, liver, colon, brain, kidney, lung, stomach, testis, or colon, with a compound or agent capable of detecting mRNA, or genomic DNA, and comparing the presence of the mRNA or genomic DNA in the control sample with the presence of corin mRNA or genomic DNA in the test sample. In still another embodiment, serial analysis of gene expression, as described in U.S. Pat. No. 5,695,937, is used to detect transcript levels of corin.

In another embodiment, the methods further include contacting the control sample with a compound or agent capable of detecting corin, and comparing the presence of corin protein in the control sample with the presence of the protein in the test sample.

The disclosure also includes kits for detecting the presence of corin in a biological sample. For example, the kit can include a compound or agent capable of detecting corin protein, e.g., an antibody, or mRNA, e.g., a nucleic acid probe, and a standard. The compound or agent can be packaged in a suitable container. The kit can further include instructions for using the kit to evaluate a subject, e.g., for risk or predisposition to a hair growth-related disorder.

It is also possible to evaluate other markers of DP cells to verify identification of a DP cell. For example, DP cells in the anagen phase expresss veriscan. A transgenic mouse line that specifically expresses green fluorescent protein (GFP) under control of the veriscan promoter can be generated, e.g., as described in Kishimoto et al. (1999) Proc. Natl. Acad. Sci USA 96:7336-7341. Isolated transgenic anagen hair follicles show GFP fluorescence from the veriscan reporter in the DP cells. The versican-GFP transgene is active during anagen but is shut off during catagen and telogen of hair growth. In certain embodiments, a cell is evaluated for both corin and versican expression, e.g., using one or more antibodies and/or one or more reporter genes.

Isolating DP Cells

DP cells can be isolated using a variety of routine techniques. For example, DP cells isolated using a corin protein binding agent (e.g., an anti-corin antibody).

For example, an anti-corin antibody described herein can be used to label DP cells in order to facilitate separation of DP cells from non-DP cells, e.g., by flow cytometry (see, e.g., Herzenberg et al. (1979) Proc. Natl. Acad. Sci. USA 76:1453-1455; Iverson et al. (1981) Prenatal Diagnosis 1:61-73; and Bianchi et al. (1991) Prenatal Diagnosis 11:523-528), micromanipulation, or attachment to an insoluble support.

Flow cytometry can utilize fluorescence-activated cell sorting (FACS) (see, e.g., Herzenberg et al. (1979) Proc. Natl. Acad. Sci. USA 76:1453), magnetic-activated cell sorting (MACS) (see, e.g., Ganshirt-Ahlert et al. (1992) Am. J. Obstet. Gynecol. 166:1350), or a combination of both procedures (Ganshirt-Ahlert et al. (1992) Am. J. Hum. Genet. 51:A48). In addition, a combination of gradient centrifugation and flow cytometry methods can also be used to increase the isolation or sorting efficiency. Other routine cell separation techniques, e.g., immunochromatography (see, e.g., U.S. Pat. No. 6,069,014), can also be used.

These and other cell separation methods can be used to separate at least one corin-expressing cell from a population of cells, e.g., a population that includes both corin-expressing and non-expressing cells. For example, the population can be obtained from natural or artificial skin, e.g., by trypsinizing such cells.

Culturing DP Cells

Following the isolation, DP cells can be maintained in a culture medium using routine methods. A suitable medium can be, e.g., a commercially available medium such as Ham's F10 (Sigma), Minimal Essential Medium ([MEM], Sigma), RPMI-1640 (Sigma), Iscove's Modified Dulbecco's Medium (IMDM), and Dulbecco's Modified Eagle's Medium ([DMEM], Sigma). In addition, any of the media described in Ham and Wallace (1979) Meth. Enz. 58:44; Barnes and Sato (1980) Anal. Biochem. 102:255; U.S. Pat. Nos. 4,767,704; 4,657,866; 4,927,762; 4,560,655; or 5,122,469; WO 90/03430; WO 87/00195; or U.S. Pat. No. Re. 30,985 may be used as culture medium for the cells. In the methods described herein, DMEM is preferably used. The medium can be supplemented as necessary with serum (such as fetal bovine serum, calf serum, or horse serum), hormones and/or other growth factors (such as insulin, transferrin, or epidermal growth factor), ions (such as sodium, chloride, calcium, magnesium, and phosphate), buffers (such as HEPES), nucleosides (such as adenosine and thymidine), trace elements (defined as inorganic compounds usually present at final concentrations in the micromolar range), and glucose or an equivalent energy source. In the methods described herein, the medium is preferably supplemented with fetal bovine serum.

The isolated cells can be cultured in a manner that maintains the hair inductive capacity of the cells or competence to express corin. In some cases, corin-expressing cells reduce or stop expressing corin under certain culture conditions. However, such cells remain competent to express corin, e.g., when contacted to keratinocytes. Such cells can be expanded in culture, and then used, e.g., to stimulate hair growth.

In one embodiment, prior to their use, an aliquot of one or more cells is evaluated, e.g., for quality control purposes to determine if the cell in the aliquot is expressing corin and/or competent to express corin, e.g., when contacted to a keratinocyte.

In one embodiment, isolated cells are cultured in the presence of at least one factor (such as a hormone or growth factor), e.g., a factor that can maintain the hair inductive capacity of the DP cells, e.g., a Wnt polypeptide (e.g., Wnt 3, Wnt4, or Wnt7) or an agent that induces or mimics an effect of Wnt-promoted signal transduction (US 2004-0170611). An agent that mimics an effect of or induces Wnt-promoted signal transduction may include, e.g., an agent that inhibits β-catenin phosphorylation, an agent that inhibits GSK3β kinase, lithium chloride, an agent that increases cytoplasmic accumulation of β-catenin, or an agent that interacts with a Frizzled receptor.

Wnt polypeptides can be obtained in several ways including isolation of Wnt or expression of a sequence encoding Wnt by genetic engineering methods. The nucleotide sequences of various Wnt proteins from various species are known. See, e.g., Gavin et al. (1990) Genes Dev. 4:2319-2332; Lee et al. (1995) Proc. Natl. Acad. Sci USA 92:2268-2272; and, Christiansen et al. (1995) Mech. Dev. 51:341-350 (describing, e.g., murine Wnt1, Wnt2, Wnt3a, Wnt3b, Wnt4, Wnt5a, Wnt 5b, Wnt6, Wnt7a, Wnt7b, Wnt8a, Wnt8b, Wnt10b, Wnt11, Wnt12) and VantVeer et al. (1984) Mol. Cell Biol. 4:2532-2534; Wainwright et al. (1988) EMBO J. 7:1743-1748; and, WO 95/17416 (describing, e.g., human Wnt1, Wnt2, Wnt3, Wnt4, Wnt5a, Wnt7a and Wnt7b).

Cells can be cultured with purified or partially purified Wnt protein (e.g., in its mature form) or with feeder cells that express Wnt, e.g., feeder cells expressing Wnt 3a, 4, 5a or 7a. For example, the cells can be cultured with Wnt for at least one, two, three, four, or five days, e.g., about a week.

In the Wnt signaling pathway, Wnt, which is a soluble molecule, binds Frizzled (Frz), a cell surface receptor, found on various types of cells. In the presence of dissheveled, binding of Wnt to Frz results in the inhibition of GSK3beta mediated phosphorylation and subsequent phosphorylation-dependent degradation of beta-catenin. Thus, Wnt binding stabilizes cellular beta-catenin. In the presence of Wnt binding, beta-catenin accumulates in the cytoplasm and binds to Lef1. The beta-catenin-Lef1 complex then translocates to the nucleus, where it mediates transcriptional activation.

The term "effects of Wnt-promoted signal transduction" refers to one or more of the biochemical effects (e.g., modulation of e.g., protein binding interactions, phosphorylation or transcription) in a cell, e.g., a DP or other corin-expressing or corin expression competent cell, initiated by Wnt signaling, e.g., by Wnt binding to Frizzled. Effects of Wnt promoted signal transduction can include Wnt binding to Frizzled; inhibition of GSK3beta mediated phosphorylation; inhibition of phosphorylation-dependent degradation of beta-catenin; accumulation of beta-catenin protein in the cytoplasm; stabilization of cellular beta-catenin; beta-catenin accumulation in the cytoplasm; beta-catenin binding to Lef1; translocation of the beta-catenin-Lef1 complex to the nucleus; and stimulation of transcription from associated genes. Components of Wnt-promoted signal transduction can include Frizzled protein, e.g., Frizzled-7 (frz-7), disheveled proteins, e.g., disheveled-2 (dsh-2), GSK3, beta catenin, Lef1, and Lef/TFC. Other effects and components of the Wnt signaling pathway are described in Arias et al. (1999) Curr. Opin. Genet. & Dev. 9:447-454.

Stimulating Hair Growth

The disclosure also provides methods of stimulating hair growth in which cultured dermal papilla cells with hair-inductive ability are transplanted into a subject, e.g., into the skin of the subject, e.g., into a hair follicle. For example, corin-expression competent skin cells can be administered to a subject, e.g., as a component of new skin or by insertion into hair follicles, e.g., existing or new hair follicles. Such corin-expression competent skin cells can express corin, e.g., after administration, e.g., when in contact with keratinocytes or signals from keratinocytes.

In some embodiments, cultured DP cells described herein are subjected to physical and/or biochemical aggregation in order to induce and/or maintain aggregation of the cultured DP cells within the transplantation site. For example, the cultured DP cells can be aggregated through centrifugation of the culture. In addition there can be added to the cultured DP cells, either prior to or at the time of transplantation into the subject, a suitable aggregation enhancing substance, e.g., a glycoprotein such as fibronectin or glycosaminoglycans, e.g., dermatan sulphate, chondroitin sulphates, proteoglycans, heparan sulphate; other extracellular matrix components known to bind DP cells, e.g., collagens; hormones; and growth factors known to induce aggregation.

The cultured DP cells can be transplanted into a subject using routine methods, e.g., those described by Jahoda et al. (1984) Nature 311:560-562. Various routes of administration and various sites can be used. For example, the cultured DP cells can be introduced directly between the dermis and the epidermis of the outer skin layer at a treatment site. This can be effected by raising a blister on the skin at the treatment site and introducing the cultured DP cells inside the blister, i.e., into the cavity occupied by the blister fluid. The blister may be raised by routine techniques, e.g., by mechanical means such as the application of a reduced pressure suction to the skin, or by chemical means.

The cultured DP cells can also be introduced into a suitable incision extending through the epidermis down into the dermis. The incision can be made using routine techniques, e.g., using a scalpel or hypodermic needle. The incision may be filled with cultured DP cells generally up to a level in direct proximity to the epidermis at either side of the incision.

Alternatively, the cultured DP cells can be introduced into a hair follicle. The hair follicle can first be exposed by a suitable incision prior to introduction of the cultured DP cells. Alternatively, the hair follicle can be filled with the cultured DP cells without first exposing it using, e.g., a hypodermic needle or other suitable delivery device.

The cultured DP cells can also be introduced into the subject together with a different type of cell, e.g., a cultured epidermal cell. The epidermal cell can be derived from the subject, from another subject, or from commercial sources. The cultured epidermal cell can either be in the form of a free epidermal cell or in the form of a sheet of epidermal cells. In the latter case, the cultured DP cells can be enclosed in a pocket formed from the sheet of epidermal cells. Where the cultured DP cells are introduced inside a pocket formed of epidermal cells, the incision in the skin at the treatment site can be formed so as to extend obliquely at a more or less shallow angle to the surface of the skin so as to form in effect a flap of skin under which the pocket of cultured dermal papilla cells can be introduced, the flap then being positioned back over the top of the pocket to seal it in and protect it from external contamination.

In another embodiment, a plurality of small closely spaced openings is formed in the skin into which the cultured DP cells are transplanted. For example, the plurality can include at least 10, 50, 100, 500, or 1000 openings. Each opening can be filled with a large plurality of cultured DP cells. The size and depth of the openings can be varied. The lateral extent of individual openings can be minimized, e.g., limited to about 5 mm, e.g., to about 2 mm. The depth of the openings can be greater than the full depth of the epidermis, e.g., extends at least 1 mm, e.g., at least 3 mm into the dermis. The openings in the skin can be formed by routine techniques and can include the use of a skin-cutting instrument, e.g., a scalpel or a hypodermic needle or a laser (e.g., a low power laser). Alternatively, a multiple-perforation apparatus can be used having a plurality of spaced cutting edges formed and arranged for simultaneously forming a plurality of spaced openings in the skin. The cultured DP cells can be introduced simultaneously into a plurality, e.g., at least several, openings in the skin.

The number of cells introduced into each opening can vary depending on various factors, e.g., the size and depth of the opening and the overall viability and activity of the cells. The number of cells introduced can be, e.g.; 1000 to 1,000,000 cells, e.g., 10,000 to 200,000 cells per opening in a volume of, e.g., 0.5 to 50 μL.

In some embodiments, the subject is treated, topically and/or systematically, with a hair growth promoting substance before, at the same time as, and/or after the transplantation of cultured DP cells to enhance hair growth. Suitable hair growth promoting substances can include, e.g., minoxidil (available from the Upjohn Co. of Kalamazoo, Mich.), cyclosporin, and natural or synthetic steroid hormones and their enhancers and antagonists, e.g., anti-androgens.

The cultured DP cells transplanted into a subject can be derived from DP cells taken from the subject. In some embodiments, DP cells are obtained from another subject of the same species or from a different species. Use of cultured DP cells derived from another subject may require administration of an immunosuppressant, alteration of histocompatibility antigens, or use of a barrier device to prevent rejection of the implanted cells.

Cultured DP cells can be administered alone or in conjunction with a barrier or agent for inhibiting immune responses against the transplanted DP cells in a recipient subject. For example, an immunosuppressive agent can be administered to a subject to inhibit or interfere with normal response in the subject. The immunosuppressive agent can be an immunosuppressive drug that inhibits T cell/or B cell activity in the subject. Examples of immunosuppressive drugs are commercially available (e.g., cyclosporin A from Sandoz Corp. East Hanover, N.J.).

An immunosuppressive agent, e.g., drug, can be administered to a subject at a dosage sufficient to achieve the desired therapeutic effect (e.g., inhibition of rejection of the cells). Suitable dosage ranges for immunosuppressive drugs can include, e.g., those described in Freed et al. (1992) N. Engl. J. Med. 327:1549; Spencer et al. (1992) N. Engl. J. Med. 327: 1541; and Widner et al. (1992) N. Engl. J. Med. 327:1556. Dosage values may vary according to factors such as age, sex, and weight of the subject.

The immunosuppressive agent can also be an antibody, an antibody fragment, or an antibody derivative that inhibits T cell activity in the subject. Antibodies capable of depleting or sequestering T cells can be, e.g., polyclonal antisera, e.g., anti-lymphocyte serum; and monoclonal antibodies; e.g., monoclonal antibodies that bind to CD2, CD3, CD4, CD8 or CD40 on the T cell surface. Such antibodies are commercially available, e.g., from American Type Culture Collection, e.g., OKT3 (ATCC CRL 8001). An antibody can be administered for an appropriate time, e.g., at least 7 days, e.g., at least 10 days, e.g., at least 30 days, to inhibit rejection of cultured DP cells following transplantation. Antibodies can be administered intravenously in a pharmaceutically acceptable carrier, e.g., saline solution.

An exemplary reconstitution method is described in Kishimoto et al. (1999) Proc. Natl. Acad. Sci USA 96:7336-7341. Primary keratinocytes were prepared from 2 newborn pups per graft and combined with $2 \times 10^6$ DP cells in the graft chamber. Hair growth was monitored two weeks after grafting and weekly thereafter. The method can be extended to other animals, e.g., humans.

Corin-expression competent cells can also be administered with other cells, e.g., non-corin expression competent cells, e.g., keratinocytes or fibroblasts. For example, they can be administered as a component of a skin graft, e.g., a natural or artificial skin graft. The corin-expression competent cells can be seeded randomly or at regular positions within the graft. An example of an artificial skin graft is an artificial dermis prepared by using polyglactin, e.g., described in U.S. Pat. No. 5,460,939. See also, e.g., U.S. 2004-0171145 and Bannasch H et al. *Clin Plast Surg.* 2003 October; 30(4):573-9.

Transgenic Animals

Methods for generating non-human transgenic animals can involve introducing the nucleic acid of interest, e.g. corin gene, into the germ line of a non-human animal to make a transgenic animal. Although rodents, e.g., rats, mice, rabbits and guinea pigs, are preferred, other non-human animals can be used. For example, one or several copies of the nucleic acid of interest may be incorporated into the DNA of a mammalian embryo by standard transgenic techniques (see, e.g., Nagy et al. *Manipulating the Mouse Embryo: A Laboratory Manual* (3rd ed. 2003)). A protocol for the production of a transgenic rat can be found in Bader et al; (1996) Clin. Exp. Pharmacol. Physiol. Suppl. 3:S81-87.

Transgenic mice containing a corin gene promoter-corin gene transgene may be generated by established methods. Other expression control sequences may direct expression of corin gene, or a functional fragment or variant thereof, to a cell type substantially lacking endogenous corin, e.g., a promoter described in Pan et al., 2002, J. Biol. Chem. 277:38390-38398. For example, the expression control sequence directs corin gene expression to DP cells.

Identifying an Agent that Modulates Corin Gene Expression or Corin Activity or Level Numerous methods exist for evaluating whether an agent alters corin gene expression or corin activity or level. In one embodiment, the ability of a test agent to modulate, e.g., increase or decrease, e.g., permanently or temporarily, expression from a corin gene promoter is evaluated by e.g., routine reporter (e.g., LacZ or GFP) transcription assay. For example, a cell or transgenic animal whose genome comprises a reporter gene operably linked to a corin gene promoter (see, e.g., Pan et al., 2002, J. Biol. Chem. 277:38390-38398), can be contacted with a test agent, and the ability of the test agent to increase or decrease reporter activity is indicative of the ability of the agent to modulate hair growth. In another embodiment, the ability of a test agent to modulate corin gene expression, or corin activity or level, is evaluated in a transgenic animal, for example, the transgenic animal described herein.

The effect of a test agent on corin gene expression or corin activity or level may also be evaluated in a cell, cell lysate, co-culture comprising a DP cell and a non-DP cell, or subject, preferably a non-human experimental mammal, and more preferably a rodent (e.g., a rat, mouse, or rabbit), or explant (e.g., skin) thereof. Methods of assessing corin gene expression are well know in the art, e.g., northern analysis, ribonuclease protection assay, reverse transcription-polymerase chain reaction (RT-PCR) or RNA in situ hybridization (see, e.g., Sambrook et al. *Molecular Cloning: A Laboratory Manual* ($3^{rd}$ ed. 2001)). The level of corin may be monitored by, e.g., western analysis, immunoassay, or in situ hybridization. Corin activity, e.g., altered promoter binding and/or transcription activity, may be determined by, e.g., electrophoretic mobility shift assay, DNA footprinting or reporter gene assay. For example, the effect of a test agent on corin gene expression or corin activity or level is observed as a change in hair growth-inducing ability of the cell, e.g., DP cell, cell extract, or co-culture, hair growth in an explant, or hair growth in a subject. For example, the effect of a test agent on corin gene expression or corin activity or level is evaluated on a transgenic cell or non-human animal, or explant or cell derived therefrom, having altered hair growth ability, as compared to a wild-type cell or non-human animal, or explant or cell derived therefrom.

The test agent may be administered to a cell, cell extract, explant or subject expressing a transgene comprising the corin gene promoter fused to lacZ. (See, e.g., Pan et al., 2002, J. Biol. Chem. 277:38390-38398.) Enhancement or inhibition of transgene, e.g., a reporter, e.g., lacZ or GFP, transcription, as a result of an effect of the test agent on the corin gene promoter or factors regulating transcription from the corin gene promoter, may be easily observed as a change in color. Reporter transcript levels, and thus corin gene promoter activity, may be monitored by established methods, e.g., northern analysis, ribonuclease protection assay, reverse transcription-polymerase chain reaction (RT-PCR) or RNA in situ hybridization (see, e.g., Cuncliffe et al. (2002) Mamm. Genome 13:245). Agents may be evaluated using a cell-free system, e.g., an environment comprising the corin gene promoter-reporter transgene (e.g., corin gene promoter-lacZ transgene), transcription factors binding the corin gene promoter, a crude cell lysate or nuclear extract, and the test agent (e.g., an agent described herein), wherein an effect of the agent on corin gene promoter activity is detected as a color change.

Assaying for Hair Growth

Modulation of hair growth, e.g., by an agent, can be measured, e.g., using the mouse vibrissa organ culture system assay. In this exemplary assay, whisker pads are isolated from mice and shortly immersed in 70% ethanol in phosphate-buffered saline (PBS), followed by a 10 minute incubation in William's E medium containing 400 U/mL penicillin, 400 µg/mL streptomycin, and 1.0 µg/mL fungizone (all from GibcoBRL). Vibrissa follicles in the anagen growth phase are isolated under a dissecting microscope, and the part of the vibrissa shaft that extends over the epidermal surface is cut off. Vibrissa follicles are incubated on MILLIPORE™ membranes in William's E medium alone or in medium containing an agent, e.g., an agent described herein. The media is replaced by fresh media, e.g., after 2 days, and the follicles incubated, e.g., for 4 days. After the incubation period, the length of the outgrowing hair shafts is measured, e.g., by image analysis of digital pictures, taken under a microscope. The lengths of hair shafts of agent-treated vibrissa follicles are compared to a control, e.g., non-agent treated vibrissa follicles, and agents are identified that modulate hair growth compared to a control.

Subjects in Need of Modulated Hair Growth and Methods of Treatment

Many subjects are in need of modulated hair growth. Subjects with hair growth-related disorders, such as alopecia, may require treatment that promotes hair growth. Normal subjects who experience or anticipate hair loss can also be treated, e.g., male subject who experience or anticipate male-pattern hair loss.

Subjects with an excess of hair growth may require treatment that inhibits hair growth. For example, corin-expressing DP cells can be targetted, e.g., inhibited or ablated, to reduce hair growth. The identification of a subject in need of modulated hair growth can be performed by the subject, a health care provider, or another party.

The subject may be supplied with a composition affecting, e.g., corin expression, by a health care provider, cosmetics retailer or another party. Instructions for using a composition described herein may be provided by a health care provider, cosmetics retailer or another party. A kit including a composition described herein and instructions for using the composition may be provided by a health care provider, cosmetics retailer or another party.

Administration

An agent described herein may be administered systemically or locally, e.g., topically. Topical administration of an agent described herein is the preferred route of administration. For topical application, the compositions of the present disclosure can include a medium compatible with a cell, explant or subject. Such topical pharmaceutical compositions can exist in many forms, e.g., in the form of a solution, cream, ointment, gel, lotion, shampoo, soap or aerosol. A wide variety of carrier materials can be employed in the hair growth modulating composition described herein, such as alcohols, aloe vera gel, allantoin, glycerin, vitamin A and E oils, mineral oils, and polyethylene glycols. Other additives, e.g., preservatives, fragrance, sunscreen, or other cosmetic ingredients, can be present in the composition.

An exemplary vehicle for topical delivery is liposomes. Liposomes can be used to carry and deliver an agent, e.g., a agent described herein, into a cell. Detailed guidance can be found in, e.g., Yarosh et al. (2001) Lancet 357: 926 and Bouwstra et al. (2002) Adv. Drug Deliv. Rev. 54 Suppl 1:S41.

For systemic administration the agent may be administered via the orally route or the parenteral route, including subcutaneously, intraperitoneally, intramuscularly, intravenously or other route. For local administration, they are administered topically, transdermally, transmucosally, intranasally or other route. A cell may be contacted extracellularly or intracellularly with the agent, e.g., by microinjection or transfection. The agent may be applied and removed immediately, applied and not removed, and/or repeatedly applied with constant, increasing or decreasing frequency and/or at increasing or decreasing doses or concentrations. More than one route of administration may be used simultaneously, e.g., topical administration in association with oral administration. Examples of parenteral dosage forms include aqueous solutions of the active agent, in a isotonic saline, 5% glucose or other well-known pharmaceutically acceptable excipient. Solubilizing agents such as cyclodextrins, or other solubilizing agents well known to those familiar with the art, can be utilized as pharmaceutical excipients for delivery of the pigment modulating composition.

The composition may be provided as, e.g., a cosmetics, a medication or a skin care product. The composition can also be formulated into dosage forms for other routes of administration utilizing conventional methods. A pharmaceutical composition can be formulated, for example, in dosage forms for oral administration as a powder or granule, or in a capsule, a tablet (each including timed release and sustained release formulations), or a gel seal, with optional pharmaceutical carriers suitable for preparing solid compositions, such as vehicles (e.g., starch, glucose, fruit sugar, sucrose, gelatin and the like), lubricants (e.g., magnesium stearate), disintegrators (e.g., starch and crystalline cellulose), and binders (e.g., lactose, mannitol, starch and gum arabic). When the composition is an injection, for example, solvents (e.g., distilled water for injection), stabilizers (e.g., sodium edetate), isotonizing agents (e.g., sodium chloride, glycerin and mannitol), pH-adjusting agents (e.g., hydrochloric acid, citric acid and sodium hydroxide), suspending agents (e.g., methyl cellulose) and the like may be used.

The hair growth modulating agent may contain other pharmaceutical ingredients, e.g., a second treatment for hair growth, e.g., minoxidil (available from the Upjohn Co. of Kalamazoo, Mich.), cyclosporin, and natural or synthetic steroid hormones and their enhancers and antagonists, e.g., anti-androgens.

Measurement of Hair Growth

The effect of an agent on hair growth can be evaluated qualitatively, e.g., by visual inspection. Qualitative indicia can include a change in hair thickness or hair length. All, most or some of the areas of the subject treated with the test agent may be affected. A treated subject may be compared with an untreated subject. For example, a treated region and an untreated region of the same subject are compared.

The effect of an agent on hair growth may also be evaluated quantitatively, e.g., by microscopic or computer-assisted measurements of hair growth. The number of hairs per given area may be determined. The evaluation may include entering a value for the evaluation, e.g., a value for the extent of change in hair growth into a database or other record. The party measuring and/or recording hair growth may be the care provider, the subject or another party.

Gene Therapy

The nucleic acids described herein, e.g., an antisense nucleic acid described herein or a nucleic acid encoding corin polypeptide, a fragment thereof, or a reporter gene that is operatively linked to a corin regulatory sequence, can be incorporated into a gene construct to be used as a part of a gene therapy protocol to deliver nucleic acids into isolated cells or into cells of an organism.

The disclosure features expression vectors for in vitro or in vivo transfection and expression of a corin polypeptide described herein in particular cell types, e.g., DP cells. Expression constructs of such components may be administered in any biologically effective carrier, e.g. any formulation or composition capable of effectively delivering the component gene to cells, e.g., DP cells, in vitro or in vivo. Approaches include insertion of the subject gene in viral vectors including recombinant retroviruses, adenovirus, adeno-associated virus, lentivirus, and herpes simplex virus-1, or recombinant bacterial or eukaryotic plasmids. Viral vectors transfect cells directly; plasmid DNA can be delivered with the help of, for example, cationic liposomes (lipofectin) or derivatized (e.g. antibody conjugated), polylysine conjugates, gramicidin S, artificial viral envelopes or other such intracellular carriers, as well as direct injection of the gene construct or calcium phosphate precipitation carried out in vitro or in vivo.

An exemplary approach for in vitro or in vivo introduction of nucleic acid into a cell, e.g., a DP cell, is by use of a viral vector containing nucleic acid, e.g. a cDNA. Infection of cells with a viral vector has the advantage that a large proportion of the targeted cells can receive the nucleic acid. Additionally, molecules encoded within the viral vector, e.g., by a cDNA contained in the viral vector, are expressed efficiently in cells that have taken up viral vector nucleic acid.

Retrovirus vectors and adeno-associated virus vectors can be used as a recombinant gene delivery system for the transfer of exogenous genes in vitro or in vivo, particularly into humans. These vectors provide efficient delivery of genes into cells, and the transferred nucleic acids are stably integrated into the chromosomal DNA of the host. The development of specialized cell lines (termed "packaging cells") that produce only replication-defective retroviruses has increased the utility of retroviruses for gene therapy, and defective retroviruses are characterized for use in gene transfer for gene therapy purposes (for a review see Miller, A. D. (1990) Blood 76:271). A replication defective retrovirus can be packaged into virions that can be used to infect a target cell, e.g., a DP cell, through the use of a helper virus by standard techniques. Protocols for producing recombinant retroviruses and for infecting cells in vitro or in vivo with such viruses can be found in Current Protocols in Molecular Biology, Ausubel, F. M. et al. (eds.) Greene Publishing Associates, (1989), Sections 9.10-9.14 and other standard laboratory manuals. Examples of suitable retroviruses include pLJ, pZIP, pWE and pEM, which are known to those skilled in the art. Examples of suitable packaging virus lines for preparing both ecotropic and amphotropic retroviral systems include ΨCrip, ΨCre, Ψ2 and ΨAm. Retroviruses have been used to introduce a variety of genes into many different cell types, including epithelial cells, in vitro and/or in vivo (see for example Eglitis, et al. (1985) Science 230:1395-1398; Danos and Mulligan (1988) Proc. Natl. Acad. Sci. USA 85:6460-6464; Wilson et al. (1988) Proc. Natl. Acad. Sci. USA 85:3014-3018; Armentano et al. (1990) Proc. Natl. Acad. Sci. USA 87:6141-6145; Huber et al. (1991) Proc. Natl. Acad. Sci. USA 88:8039-8043; Ferry et al. (1991) Proc. Natl. Acad. Sci. USA 88:8377-8381; Chowdhury et al. (1991) Science 254:1802-1805; van Beusechem et al. (1992) Proc. Natl. Acad. Sci. USA 89:7640-7644; Kay et al. (1992) Human Gene Therapy 3:641-647; Dai et al. (1992) Proc. Natl. Acad. Sci. USA 89:10892-10895; Hwu et al. (1993) J. Immunol. 150:4104-4115; U.S. Pat. No. 4,868,116; U.S. Pat. No. 4,980,286; PCT Application WO 89/07136; PCT Application WO 89/02468; PCT Application WO 89/05345; and PCT Application WO 92/07573).

Another viral gene delivery system useful in the methods disclosed herein utilizes adenovirus-derived vectors. The genome of an adenovirus can be manipulated such that it encodes and expresses a gene product of interest but is inactivated in terms of its ability to replicate in a normal lytic viral life cycle. See, for example, Berkner et al. (1988) BioTechniques 6:616; Rosenfeld et al. (1991) Science 252:431-434; and Rosenfeld et al. (1992) Cell 68:143-155. Suitable adenoviral vectors derived from the adenovirus strain Ad type 5 dl324 or other strains of adenovirus (e.g., Ad2, Ad3, Ad7 etc.) are known to those skilled in the art. Recombinant adenoviruses can be advantageous in certain circumstances in that they are not capable of infecting nondividing cells and can be used to infect a wide variety of cell types, including epithelial cells (Rosenfeld et al. (1992) supra). Furthermore, the virus particle is relatively stable and amenable to purification and concentration, and, as above, can be modified so as to affect the spectrum of infectivity. Additionally, introduced adenoviral DNA (and foreign DNA contained therein) is not integrated into the genome of a host cell but remains episomal, thereby avoiding potential problems that can occur as a result of insertional mutagenesis in situ where introduced DNA becomes integrated into the host genome (e.g., retroviral DNA). Moreover, the carrying capacity of the adenoviral genome for foreign DNA is large (up to 8 kilobases) relative to other gene delivery vectors (Berkner et al. supra; Haj-Ahmand and Graham (1986) J. Virol. 57:267).

Yet another viral vector system useful for delivery of the subject gene is the adeno-associated virus (AAV). Adeno-associated virus is a naturally occurring defective virus that requires another virus, such as an adenovirus or a herpes virus, as a helper virus for efficient replication and a productive life cycle. (For a review see Muzyczka et al. (1992) Curr. Topics in Micro. and Immunol. 158:97-129). It is also one of the few viruses that may integrate its DNA into non-dividing cells, and exhibits a high frequency of stable integration (see for example Flotte et al. (1992) Am. J. Respir. Cell. Mol. Biol. 7:349-356; Samulski et al. (1989) J. Virol. 63:3822-3828; and McLaughlin et al. (1989) J. Virol. 62:1963-1973). Vectors containing as few as 300 base pairs of AAV can be packaged and can integrate. Space for exogenous DNA is limited to about 4.5 kb. An AAV vector such as that described in Tratschin et al. (1985) Mol. Cell. Biol. 5:3251-3260, can be used to introduce DNA into cells. A variety of nucleic acids have been introduced into different cell types using AAV vectors (see for example Hermonat et al. (1984) Proc. Natl. Acad. Sci. USA 81:6466-6470; Tratschin et al. (1985) Mol. Cell. Biol. 4:2072-2081; Wondisford et al. (1988) Mol. Endocrinol. 2:32-39; Tratschin et al. (1984) J. Virol. 51:611-619; and Flotte et al. (1993) J. Biol. Chem. 268:3781-3790).

In addition to viral transfer methods, such as those illustrated above, non-viral methods can also be employed to cause expression of an nucleic acid agent described herein (e.g., a nucleic acid encoding a corin polypeptide) in the tissue, e.g., the skin, e.g., DP cells, of a subject. Most nonviral methods of gene transfer rely on normal mechanisms used by mammalian cells for the uptake and intracellular transport of macromolecules. In one embodiment, non-viral gene delivery systems described herein rely on endocytic pathways for the uptake of the subject gene by the targeted cell. Exemplary gene delivery systems of this type include liposomal derived systems, poly-lysine conjugates, and artificial viral envelopes. Other embodiments include plasmid injection systems, such as are described in Meuli et al. (2001) J Invest Dermatol. 116(1):131-135; Cohen et al. (2000) Gene Ther. 7(22):1896-905; or Tam et al. (2000) Gene Ther. 7(21):1867-74.

In a representative embodiment, a gene encoding an agent described herein, e.g., corin, can be entrapped in liposomes bearing positive charges on their surface (e.g., lipofectins) and (optionally) that are tagged with antibodies against cell surface antigens of the target tissue (Mizuno et al. (1992) No Shinkei Geka 20:547-551; PCT publication WO91/06309; Japanese patent application 10473.81; and European patent publication EP-A-43075).

In clinical settings, the gene delivery systems for the therapeutic gene can be introduced into a patient by any of a number of methods, each of which is familiar in the art. For instance, a pharmaceutical preparation of the gene delivery system can be introduced systemically, e.g. by intravenous injection, and specific transduction of the protein in the target cells, e.g., DP cells, occurs predominantly from specificity of transfection provided by the gene delivery vehicle, cell-type or tissue-type expression due to the transcriptional regulatory sequences controlling expression of the receptor gene, or a combination thereof. In other embodiments, initial delivery of the recombinant gene is more limited with introduction into the animal being quite localized. For example, the gene delivery vehicle can be introduced by catheter (see U.S. Pat. No. 5,328,470) or by stereotactic injection (e.g. Chen et al. (1994) PNAS 91: 3054-3057).

The pharmaceutical preparation of the gene therapy construct can consist essentially of the gene delivery system in an acceptable diluent, or can comprise a slow release matrix in which the gene delivery vehicle is imbedded. Alternatively, where the complete gene delivery system can be produced intact from recombinant cells, e.g. retroviral vectors, the pharmaceutical preparation can comprise one or more cells that produce the gene delivery system.

Cell Therapy

Hair growth can also be modulated in a subject by introducing into a cell, e.g., a skin cell such as a DP cell, a nucleotide sequence that encodes a corin polypeptide. The nucleotide sequence can be a corin encoding sequence or active fragment thereof, and any of: a promoter sequence, e.g., a promoter sequence from a corin gene or from another gene; an enhancer sequence, e.g., 5' untranslated region (UTR), e.g., a 5' UTR from a corin gene or from another gene, a 3' UTR, e.g., a 3' UTR from a corin gene or from another gene; a polyadenylation site; an insulator sequence; or another sequence that modulates the expression of corin. The cell, e.g., a DP cell, can then be introduced into the subject. Many other embodiments, however, do not require genetic modification of DP cells.

Primary and secondary cells to be genetically engineered can be obtained from a variety of tissues, e.g., skin, and include cell types, e.g., DP cells, that can be maintained and propagated in culture. For example, primary and secondary cells include mesenchymal cells, e.g., DP cells; adipose cells; fibroblasts; keratinocytes; epithelial cells, e.g., mammary epithelial cells and intestinal epithelial cells; endothelial cells; glial cells; neural cells; formed elements of the blood, e.g., lymphocytes, and bone marrow cells; muscle cells; and precursors of these somatic cell types. Primary cells can be obtained from the individual to whom the genetically engineered primary or secondary cells are administered. However, primary cells may be obtained from a donor. Primary cells useful in the methods described herein can be derived from mammals, e.g., mice, rats, sheep, dogs, or primates, e.g., humans or monkeys, e.g., chimpanzees.

The term "primary cell" includes cells present in a suspension of cells isolated from a vertebrate tissue source, cells present in an explant derived from tissue, both of the previous types of cells plated for the first time, and cell suspensions derived from these plated cells. The term "secondary cell" or "cell strain" refers to cells at all subsequent steps in culturing.

Primary or secondary cells of vertebrate, particularly mammalian, origin can be transfected with an exogenous nucleic acid sequence that includes a nucleic acid sequence encoding a reporter peptide, and/or a heterologous nucleic acid sequence, e.g., a nucleic acid sequence encoding corin or an agonist or antagonist thereof, and produce the encoded product stably and reproducibly in vitro and in vivo, over extended periods of time. A heterologous nucleic acid sequence can also be a regulatory sequence, e.g., a promoter, that causes expression, e.g., inducible expression or upregulation, of an endogenous sequence. An exogenous nucleic acid sequence can be introduced into a primary or secondary cell by homologous recombination as described, for example, in U.S. Pat. No. 5,641,670, the contents of which are incorporated herein by reference. The transfected primary or secondary cells may also include DNA encoding a selectable marker that confers a selectable phenotype upon them, facilitating their identification and isolation.

Vertebrate tissue can be obtained by standard methods such a punch biopsy or other surgical methods of obtaining a tissue source of the primary cell type of interest. For example, punch biopsy is used to obtain skin as a source of mesenchymal cells, e.g., DP cells, fibroblasts, or keratinocytes. A mixture of primary cells is obtained from the tissue, using known methods, such as enzymatic digestion or explanting. If enzymatic digestion is used, enzymes such as collagenase, hyaluronidase, dispase, pronase, trypsin, elastase and chymotrypsin can be used. DP cells can be further isolated using the methods described herein.

The resulting primary cells, e.g., DP cells, can be transfected directly or can be cultured first, removed from the culture plate and resuspended before transfection is carried out. Primary cells or secondary cells are combined with exogenous nucleic acid sequence to, e.g., stably integrate into their genomes, and treated in order to accomplish transfection. As used herein, the term "transfection" includes a variety of techniques for introducing an exogenous nucleic acid into a cell, including calcium phosphate or calcium chloride precipitation, microinjection, DEAE-dextrin-mediated transfection, lipofection or electroporation, all of which are routine in the art.

The transfected cells, e.g., cells produced as described herein, can be introduced into an individual to whom the product is to be delivered. Various routes of administration and various sites (e.g., renal sub capsular, subcutaneous, central nervous system (including intrathecal), intravascular, intrahepatic, intrasplanchnic, intraperitoneal (including intraomental), intramuscularly implantation) can be used. Once implanted in an individual, the transfected cells produce the product encoded by the heterologous DNA or are affected by the heterologous DNA itself. For example, an individual who desires additional hair growth (e.g., in the scalp) or suffers from a hair growth-related disorder (e.g., alopecia) is a candidate for implantation of cells, e.g., DP cells, producing an agent described herein, e.g., corin polypeptide or an agent that modulates corin expression.

Diagnostic Assays

The diagnostic assays described herein involve evaluating corin levels in the subject, e.g., in skin. Various art-recognized methods are available for evaluating corin. For example, the method can include evaluating either the level of corin and/or an activity of corin. Techniques for detection of corin are known in the art and include, e.g., antibody based assays such as enzyme immunoassays (EIA), radioimmunoassays (RIA), and Western blot analysis. Typically, the level in the subject is compared to the level and/or activity in a control, e.g., the level and/or activity in a tissue from a subject lacking the disorder.

Techniques for evaluating binding activity, e.g., of corin to a corin binding partner, include fluid phase binding assays, affinity chromatography, size exclusion or gel filtration, ELISA, immunoprecipitation (e.g., the ability of an antibody specific to a first factor, e.g., corin, to co-immunoprecipitate a second factor or complex with which the first factor can associate in nature).

Another method of evaluating corin in a subject is to determine the presence or absence of a lesion in or the misexpression of a gene that encodes corin. The method can include one or more of the following: detecting, in a tissue of the subject, the presence or absence of a mutation that affects the expression of a gene encoding corin, or detecting the presence or absence of a mutation in a region that controls the expression of the gene, e.g., a mutation in the 5' control region; detecting, in a tissue of the subject, the presence or absence of a mutation that alters the structure of a gene encoding corin; detecting, in a tissue of the subject, the misexpression of a gene encoding corin, at the mRNA level, e.g., detecting a non-wild type level of a mRNA; and detecting, in a tissue of the subject, the misexpression of the gene, at the protein level, e.g., detecting a non-wild type level of a corin polypeptide.

In one embodiment, the method includes: ascertaining the existence of at least one of: a deletion of one or more nucleotides from a gene encoding corin; an insertion of one or more nucleotides into the gene, a point mutation, e.g., a substitution of one or more nucleotides of the gene, a gross chromosomal rearrangement of the gene, e.g., a translocation, inversion, or deletion.

For example, detecting the genetic lesion can include: (i) providing a probe/primer including an oligonucleotide containing a region of nucleotide sequence that hybridizes to a sense or antisense sequence from a corin gene, or naturally occurring mutants thereof or 5' or 3' flanking sequences naturally associated with the gene; (ii) exposing the probe/primer to nucleic acid of a tissue; and detecting, by hybridization, e.g., in situ hybridization, of the probe/primer to the nucleic acid, the presence or absence of the genetic lesion.

In another embodiment, detecting the misexpression includes ascertaining the existence of at least one of: an alteration in the level of a mRNA transcript of a gene encoding corin; the presence of a non-wild type splicing pattern of a mRNA transcript of the gene; or a non-wild type level of a gene encoding corin.

In another embodiment, the method includes determining the structure of a gene encoding corin, an abnormal structure being indicative of risk for the disorder.

In yet another embodiment, the method includes contacting a sample from the subject with an antibody to corin, or a nucleic acid that hybridizes specifically with the gene.

Antibodies

As used herein, the term "antibody" refers to a protein comprising at least one, and preferably two, heavy (H) chain variable domains (abbreviated herein as VH), and at least one and preferably two light (L) chain variable domains (abbreviated herein as VL). Accordingly, the term encompasses full length. IgG antibodies and fragments thereof.

The VH and VL domains can be further subdivided into regions of hypervariability, termed "complementarity determining regions" ("CDR"), interspersed with regions that are more conserved, termed "framework regions" (FR). The extent of the framework region and CDRs has been precisely defined (see, Kabat et al. (1991) *Sequences of Proteins of Immunological Interest, Fifth Edition*, U.S. Department of Health and Human Services, NIH Publication No. 91-3242, and Chothia et al. (1987) *J. Mol. Biol.* 196:901-917, which are incorporated herein by reference). Each VH and VL is composed of three CDRs and four FRs, arranged from amino-terminus to carboxy-terminus in the following order: FR1, CDR1, FR2, CDR2, FR3, CDR3, FR4. Camelid antibodies can include a single variable immunoglobulin domain.

The antibody can further include a heavy and light chain constant region, to thereby form a heavy and light immunoglobulin chain, respectively. In one embodiment, the antibody is a tetramer of two heavy immunoglobulin chains and two light immunoglobulin chains, wherein the heavy and light immunoglobulin chains are inter-connected by, e.g., disulfide bonds. The heavy chain constant region is comprised of three domains, CH1, CH2 and CH3. The light chain constant region is comprised of one domain, CL. The variable domain of the heavy and light chains contains a binding domain that interacts with an antigen. The constant regions of the antibodies typically mediate the binding of the antibody to host tissues or factors, including various cells of the immune system (e.g., agonist cells) and the first component (Clq) of the classical complement system.

As used herein, the term "immunoglobulin" refers to a protein that includes one or more polypeptides that have a domain that forms an immunoglobulin fold.

An immunoglobulin can include a region encoded by an immunoglobulin gene. The recognized human immunoglobulin genes include the kappa, lambda, alpha (IgA1 and IgA2), gamma (IgG1, IgG2, IgG3, IgG4), delta, epsilon and mu constant region genes, as well as the myriad immunoglobulin genes and gene segments. Full-length immunoglobulin "light chains" (about 25 kDa or 214 amino acids) are encoded by a variable region gene at the $NH_2$-terminus (about 110 amino acids) and a kappa or lambda constant region gene at the COOH-terminus. Full-length immunoglobulin "heavy chains" (about 50 kDa or 446 amino acids) are similarly encoded by a variable region gene (about 116 amino acids) and one of the other aforementioned constant region genes, e.g., gamma (encoding about 330 amino acids). As used herein, "isotype" refers to the antibody class (e.g., IgM, IgG1, IgG2, IgG3, IgG4) that is encoded by heavy chain constant region genes.

The term "antigen-binding fragment" of an antibody (or simply "antibody portion," or "fragment"), as used herein, refers to one or more fragments of a full-length antibody that retain the ability to specifically bind to an antigen (e.g., a corin) Examples of binding fragments encompassed within the term "antigen-binding fragment" of an antibody include (i) a Fab fragment, a monovalent fragment consisting of the VL, VH, CL and CH1 domains; (ii) a F(ab')$_2$ fragment, a bivalent fragment comprising two Fab fragments linked by a disulfide bridge at the hinge region; (iii) a Fd fragment consisting of the VH and CH1 domains; (iv) a Fv fragment consisting of the VL and VH domains of a single arm of an antibody, (v) a dAb fragment (Ward et al., (1989) *Nature* 341:544-546), which consists of a VH domain; and (vi) an isolated complementarity determining region (CDR). Furthermore, although the two domains of the Fv fragment, VL and VH, are coded for by separate genes, they can be joined, using recombinant methods, by a synthetic linker that enables them to be made as a single protein chain in which the VL and VH domains pair to form monovalent molecules (known as single chain Fv (scFv); see, e.g., Bird et al. (1988) *Science* 242:423-426; and Huston et al. (1988) *Proc. Natl. Acad. Sci. USA* 85:5879-5883). Such single chain antibodies are also intended to be encompassed within the term "antigen-binding fragment" of an antibody. These antibody fragments are obtained using conventional techniques known to those with skill in the art, and the fragments are screened for utility in the same manner as are intact antibodies. An "effectively human" immunoglobulin variable domain is an immunoglobulin variable domain that includes a sufficient number of human framework amino acid positions such that the immunoglobulin variable domain does not elicit an immunogenic response in a normal human. An "effectively human" antibody is an antibody that includes a sufficient number of human amino acid positions such that the antibody does not elicit an immunogenic response in a normal human. Human and effectively human immunoglobulin variable domains and antibodies can be used.

Antibodies can be made by immunizing an animal (e.g., non-human animals and non-human animals include human immunoglobulin genes) with the relevant antigen or fragments thereof. Such antibodies may be obtained using the entire mature protein as an immunogen, or by using fragments (e.g., soluble fragments and small peptides). The peptide immunogens additionally may contain a cysteine residue at the carboxyl terminus, and are conjugated to a hapten such as keyhole limpet hemocyanin (KLH). Additional peptide immunogens may be generated by replacing tyrosine residues with sulfated tyrosine residues. Methods for synthesizing such peptides are known in the art, for example, as in Merrifield, *J. Amer. Chem. Soc.* 85, 2149-2154 (1963); Krstenansky et al., *FEBS Lett.* 211, 10 (1987). Antibodies can also be made by selecting antibodies from a protein expression library, e.g., a phage display library.

Human monoclonal antibodies (mAbs) directed against target proteins can be generated using transgenic mice carrying the human immunoglobulin genes rather than the mouse system. Splenocytes from these transgenic mice immunized with the antigen of interest are used to produce hybridomas that secrete human mAbs with specific affinities for epitopes from a human protein (see, e.g., WO 91/00906, WO 91/10741; WO 92/03918; WO 92/03917; Lonberg et al. 1994 *Nature* 368:856-859; Green et al. 1994 *Nature Genet.* 7:13-21; Morrison et al. 1994 *Proc. Natl. Acad. Sci. USA* 81:6851-6855; Bruggeman et al. 1993 *Year Immunol* 7:33-40; Tuaillon et al. 1993 *PNAS* 90:3720-3724; Bruggeman et al. 1991 *Eur J Immunol* 21:1323-1326).

Monoclonal antibodies can also be generated by other methods. An exemplary alternative method, referred to as the "combinatorial antibody display" method, has been developed to identify and isolate antibody fragments having a particular antigen specificity, and can be utilized to produce monoclonal antibodies (for descriptions of combinatorial antibody display see e.g., Sastry et al. 1989 *PNAS* 86:5728; Huse et al. 1989 *Science* 246:1275; and Orlandi et al. 1989 *PNAS* 86:3833 and phage display methods, e.g., U.S. 2002-0102613). After immunizing an animal with an immunogen as described above, the antibody repertoire of the resulting B-cell pool is cloned. Methods are generally known for obtaining the DNA sequence of the variable domains of a diverse population of immunoglobulin molecules by using a mixture of oligomer primers and PCR. For instance, mixed oligonucleotide primers corresponding to the 5' leader (signal peptide) sequences and/or framework 1 (FR1) sequences, as well as primer to a conserved 3' constant region primer can be used for PCR amplification of the heavy and light chain variable domains from a number of murine antibodies (Larrick et al., 1991, *Biotechniques* 11:152-156). A similar strategy can also been used to amplify human heavy and light chain variable domains from human antibodies (Larrick et al., 1991, *Methods: Companion to Methods in Enzymology* 2:106-110).

Chimeric antibodies, including chimeric immunoglobulin chains, can be produced by recombinant DNA techniques known in the art. For example, a gene encoding the Fc constant region of a murine (or other species) monoclonal antibody molecule is digested with restriction enzymes to remove the region encoding the murine Fc, and the equivalent portion of a gene encoding a human Fc constant region is substituted (see Robinson et al., PCT/US86/02269; EP 184 187; EP 171,496; EP 173,494; Neuberger et al., International Application WO 86/01533; Cabilly et al. U.S. Pat. No. 4,816,567; Cabilly et al., EP 125,023; Better et al. (1988 *Science* 240: 1041-1043); Liu et al. (1987) *PNAS* 84:3439-3443; Liu et al., 1987, *J. Immunol.* 139:3521-3526; Sun et al. (1987) *PNAS* 84:214-218; Nishimura et al., 1987, *Canc. Res.* 47:999-1005; Wood et al. (1985) *Nature* 314:446-449; and Shaw et al., 1988, *J. Natl Cancer Inst.* 80:1553-1559).

An antibody or an immunoglobulin chain can be humanized by methods known in the art. Humanized antibodies, including humanized immunoglobulin chains, can be generated by replacing sequences of the Fv variable domain which are not directly involved in antigen binding with equivalent sequences from human Fv variable domains. General methods for generating humanized antibodies are provided by Morrison, 1985, *Science* 229:1202-1207, by Oi et al., 1986, *BioTechniques* 4:214, and by Queen et al. U.S. Pat. No. 5,585, 089, U.S. Pat. No. 5,693,761 and U.S. Pat. No. 5,693,762, the contents of all of which are hereby incorporated by reference. Those methods include isolating, manipulating, and expressing the nucleic acid sequences that encode all or part of immunoglobulin Fv variable domains from at least one of a heavy or light chain. Sources of such nucleic acid are well known to those skilled in the art and, for example, may be obtained from a hybridoma producing an antibody against a predetermined target. The recombinant DNA encoding the humanized antibody, or fragment thereof, can then be cloned into an appropriate expression vector.

Humanized or CDR-grafted antibody molecules or immunoglobulins can be produced by CDR-grafting or CDR substitution, wherein one, two, or all CDRs of an immunoglobulin chain can be replaced. See, e.g., U.S. Pat. No. 5,225,539; Jones et al. 1986 *Nature* 321:552-525; Verhoeyan et al. 1988 *Science* 239:1534; Beidler et al. 1988 *J. Immunol.* 141:4053-4060; Winter U.S. Pat. No. 5,225,539. Winter describes a CDR-grafting method which may be used to prepare the humanized antibodies (UK Patent Application GB 2188638A, filed on Mar. 26, 1987; Winter U.S. Pat. No. 5,225,539). All or part of the CDRs of a particular human antibody may be replaced with at least a portion of a non-human CDR or only some of the CDRs may be replaced with non-human CDRs. It is only necessary to replace the number of CDRs, or portions thereof required for binding of the humanized antibody to the target antigen, e.g., a protein disclosed herein.

In some implementations, monoclonal, chimeric and humanized antibodies can be modified by, e.g., deleting, adding, or substituting other portions of the antibody, e.g., the constant region. For example, an antibody can be modified as follows: (i) by deleting the constant region; (ii) by replacing the constant region with another constant region, e.g., a constant region meant to increase half-life, stability or affinity of the antibody, or a constant region from another species or antibody class; or (iii) by modifying one or more amino acids in the constant region to alter; for example, the number of glycosylation sites, agonist cell function, Fc receptor (FcR) binding, complement fixation, among others.

Methods for altering antibody constant regions are known. Antibodies with altered function, e.g. altered affinity for an agonist ligand, such as FcR on a cell, or the C1 component of complement can be produced by replacing at least one amino acid residue in the constant portion of the antibody with a different residue (see e.g., EP 388 151, U.S. Pat. No. 5,624,821 and U.S. Pat. No. 5,648,260). Similar type of alterations could be described which if applied to the murine, or other species immunoglobulin would reduce or eliminate these functions.

To identify an antibody that not only binds, but also has a particular function (e.g., inhibits), an antibody can be evaluated in a functional assay. For example, a plurality of antibodies that bind to a target (e.g., a protein described herein) can be evaluated in this manner. Antibodies that inhibit an activity of a protein described herein, e.g., an enzymatic activity, can be selected.

Kits

An agent described herein (e.g., corin or an agent that binds to or modulates corin) can be provided in a kit. The kit includes (a) an agent, e.g., a composition that includes an agent, and (b) informational material. The informational material can be descriptive, instructional, marketing or other material that relates to the methods described herein and/or the use of corin for the methods described herein. For example, the informational material relates to hair growth.

In one embodiment, the informational material can include instructions to administer an agent described herein in a suitable manner to perform the methods described herein, e.g., in a suitable dose, dosage form, or mode of administration (e.g., a dose, dosage form, or mode of administration described herein). Preferred doses, dosage forms, or modes of administration are topical and percutaneous. In another embodiment, the informational material can include instructions to administer an agent described herein to a suitable subject, e.g., a human, e.g., a human having, or at risk for, a hair growth-related disorder.

The informational material of the kits is not limited in its form. In many cases, the informational material, e.g., instructions, is provided in printed matter, e.g., a printed text, drawing, and/or photograph, e.g., a label or printed sheet. However, the informational material can also be provided in other formats, such as Braille, computer readable material, video recording, or audio recording. In another embodiment, the informational material of the kit is contact information, e.g., a physical address, email address, website, or telephone number, where a user of the kit can obtain substantive information about corin and/or its use in the methods described herein. Of course, the informational material can also be provided in any combination of formats.

In addition to an agent described herein, the composition of the kit can include other ingredients, such as a solvent or buffer, a stabilizer, a preservative, a fragrance or other cosmetic ingredient, and/or a second agent for treating a condition or disorder described herein, e.g., minoxidil (available from the Upjohn Co. of Kalamazoo, Mich.), cyclosporin, and natural or synthetic steroid hormones and their enhancers and antagonists, e.g., anti-androgens. Alternatively, the other ingredients can be included in the kit, but in different compositions or containers than an agent described herein. In such embodiments, the kit can include instructions for admixing an agent described herein and the other ingredients, or for using an agent described herein together with the other ingredients.

An agent described herein can be provided in any form, e.g., liquid, dried or lyophilized form. An agent described herein can be substantially pure and/or sterile. When an agent described herein is provided in a liquid solution, the liquid solution can be aqueous solution, e.g., a sterile aqueous solution. When an agent described herein is provided as a dried form, reconstitution generally is by the addition of a suitable solvent. The solvent, e.g., sterile water or buffer, can optionally be provided in the kit.

The kit can include one or more containers for the composition containing an agent described herein. In some embodiments, the kit contains separate containers, dividers or compartments for the composition and informational material. For example, the composition can be contained in a bottle, vial, or syringe, and the informational material can be contained in a plastic sleeve or packet. In other embodiments, the separate elements of the kit are contained within a single, undivided container. For example, the composition is contained in a bottle, vial or syringe that has attached thereto the informational material in the form of a label. In some embodiments, the kit includes a plurality (e.g., a pack) of individual containers; each containing one or more unit dosage forms (e.g., a dosage form described herein) of an agent described herein. For example, the kit includes a plurality of syringes, ampules, foil packets, or blister packs, each containing a single unit dose of an agent described herein. The containers of the kits can be air tight and/or waterproof.

The kit optionally includes a device suitable for administration of the composition, e.g., a syringe, inhalant, pipette, forceps, measured spoon, dropper (e.g., eye dropper), swab (e.g., a cotton swab or wooden swab), or any such delivery device. In one embodiment, the device is a swab.

Generation of Variants: Production of Altered DNA and Peptide Sequences by Random Methods Amino acid sequence variants of corin polypeptides or fragments thereof can be prepared by a number of techniques, such as random mutagenesis of DNA which encodes a corin or a region thereof. Useful methods also include PCR mutagenesis and saturation mutagenesis. A library of random amino acid sequence variants can also be generated by the synthesis of a set of degenerate oligonucleotide sequences.

Exemplary variants of corin include dominant negative or hyperactive corin sequences. E.g., such variants can include corin sequences that lack one or more of the corin protease domain(s), LDL receptor domain(s), frizzled domain(s) and scavenger receptor domains(s). Other variants may have one or more "extra" domains selected from, e.g., extra corin protease domain(s), LDL receptor domain(s), frizzled domain(s) and scavenger receptor domains(s).

PCR Mutagenesis

In PCR mutagenesis, reduced Taq polymerase fidelity is used to introduce random mutations into a cloned fragment of DNA (Leung et al., 1989, *Technique* 1:11-15). This is a very powerful and relatively rapid method of introducing random mutations. The DNA region to be mutagenized is amplified using the polymerase chain reaction (PCR) under conditions that reduce the fidelity of DNA synthesis by Taq DNA polymerase, e.g., by using a dGTP/dATP ratio of five and adding $Mn^{2+}$ to the PCR reaction. The pool of amplified DNA fragments are inserted into appropriate cloning vectors to provide random mutant libraries.

Saturation Mutagenesis

Saturation mutagenesis allows for the rapid introduction of a large number of single base substitutions into cloned DNA fragments (Mayers et al., 1985, *Science* 229:242). This technique includes generation of mutations, e.g., by chemical treatment or irradiation of single-stranded DNA in vitro, and synthesis of a complimentary DNA strand. The mutation frequency can be modulated by modulating the severity of the treatment, and essentially all possible base substitutions can be obtained. Because this procedure does not involve a genetic selection for mutant fragments both neutral substitutions, as well as those that alter function, are obtained. The distribution of point mutations is not biased toward conserved sequence elements.

Degenerate Oligonucleotides

A library of homologs can also be generated from a set of degenerate oligonucleotide sequences. Chemical synthesis of a degenerate sequences can be carried out in an automatic DNA synthesizer, and the synthetic genes then ligated into an appropriate expression vector. The synthesis of degenerate oligonucleotides is known in the art (see for example, Narang, SA (1983) *Tetrahedron* 39:3; Itakura et al. (1981) *Recombinant DNA, Proc 3rd Cleveland Sympos. Macromolecules*, ed. A G Walton, Amsterdam: Elsevier pp273-289; Itakura et al. (1984) *Annu. Rev. Biochem.* 53:323; Itakura et al. (1984) *Science* 198:1056; Ike et al. (1983) *Nucleic Acid Res.* 11:477). Such techniques have been employed in the directed evolution of other proteins (see, for example, Scott et al. (1990) *Science* 249:386-390; Roberts et al. (1992) *PNAS* 89:2429-2433; Devlin et al. (1990) *Science* 249: 404-406; Cwirla et al. (1990) *PNAS* 87: 6378-6382; as well as U.S. Pat. Nos. 5,223,409, 5,198,346, and 5,096,815).

Generation of Variants: Production of Altered DNA and Peptide Sequences by Directed Mutagenesis Non-random or directed mutagenesis techniques can be used to provide specific sequences or mutations in specific regions. These techniques can be used to create variants that include, e.g., deletions, insertions, or substitutions, of residues of the known amino acid sequence of a protein. The sites for mutation can be modified individually or in series, e.g., by (1) substituting first with conserved amino acids and then with more radical choices depending upon results achieved, (2) deleting the target residue, or (3) inserting residues of the same or a different class adjacent to the located site, or combinations of options 1-3.

Alanine Scanning Mutagenesis

Alanine scanning mutagenesis is a useful method for identification of certain residues or regions of the desired protein that are preferred locations or domains for mutagenesis (see, e.g., Cunningham and Wells (1989) *Science* 244:1081-1085). In alanine scanning, a residue or group of target residues are identified (e.g., charged residues such as Arg, Asp, His, Lys, and Glu) and replaced by a neutral or negatively charged amino acid (e.g., alanine or polyalanine). Replacement of an amino acid can affect the interaction of the amino acids with the surrounding aqueous environment in or outside the cell. Those domains demonstrating functional sensitivity to the substitutions are then refined by introducing further or other variants at or for the sites of substitution. Thus, while the site for introducing an amino acid sequence variation is predetermined, the nature of the mutation per se need not be predetermined. For example, to optimize the performance of a mutation at a given site, alanine scanning or random mutagenesis may be conducted at the target codon or region and the expressed desired protein subunit variants are screened for the optimal combination of desired activity.

Oligonucleotide-Mediated Mutagenesis

Oligonucleotide-mediated mutagenesis is a useful method for preparing substitution, deletion, and insertion variants of DNA (see, e.g., Adelman et al. (1983) *DNA* 2:183). Briefly, the desired DNA is altered by hybridizing an oligonucleotide encoding a mutation to a DNA template, where the template is the single-stranded form of a plasmid or bacteriophage containing the unaltered or native DNA sequence of the desired protein. After hybridization, a DNA polymerase is used to synthesize an entire second complementary strand of the template that will thus incorporate the oligonucleotide primer, and will code for the selected alteration in the desired protein DNA. Generally, oligonucleotides of at least 25 nucleotides in length are used. An optimal oligonucleotide will have 12 to 15 nucleotides that are completely complementary to the template on either side of the nucleotide(s) coding for the mutation. This ensures that the oligonucleotide will hybridize properly to the single-stranded DNA template molecule. The oligonucleotides are readily synthesized using techniques known in the art (see, e.g., Crea et al. (1978) *Proc. Natl. Acad. Sci. USA* 75: 5765).

Cassette Mutagenesis

Another method for preparing variants, cassette mutagenesis, is based on the technique described by Wells et al. (1985) *Gene* 34:315). The starting material is a plasmid (or other vector) that includes the protein subunit DNA to be mutated. The codon(s) in the protein subunit DNA to be mutated are identified. There must be a unique restriction endonuclease site on each side of the identified mutation site(s). If no such restriction sites exist, they may be generated using the above-described oligonucleotide-mediated mutagenesis method to introduce them at appropriate locations in the desired protein subunit DNA. After the restriction sites have been introduced into the plasmid, the plasmid is cut at these sites to linearize it. A double-stranded oligonucleotide encoding the sequence of the DNA between the restriction sites but containing the desired mutation(s) is synthesized using standard procedures. The two strands are synthesized separately and then hybridized together using standard techniques. This double-stranded oligonucleotide is referred to as the cassette. This cassette is designed to have 3' and 5' ends that are comparable with the ends of the linearized plasmid, such that it can be directly ligated to the plasmid. This plasmid now contains the mutated desired protein subunit DNA sequence.

Combinatorial Mutagenesis

Combinatorial mutagenesis can also be used to generate variants. For example, the amino acid sequences for a group of homologs or other related proteins are aligned, e.g., to promote the highest homology possible. All of the amino acids that appear at a given position of the aligned sequences can be selected to create a degenerate set of combinatorial sequences. The variegated library of variants is generated by combinatorial mutagenesis at the nucleic acid level, and is encoded by a variegated gene library. For example, a mixture of synthetic oligonucleotides can be enzymatically ligated into gene sequences such that the degenerate set of potential sequences are expressible as individual peptides, or alternatively, as a set of larger fusion proteins containing the set of degenerate sequences.

Primary High-Through-Put Methods for Screening Libraries of Peptide Fragments or Homologs Various techniques are known in the art for screening peptides, e.g., synthetic peptides, e.g., small molecular weight peptides, e.g., linear or cyclic peptides, or generated mutant gene products. Techniques for screening large gene libraries often include cloning the gene library into replicable expression vectors, transforming appropriate cells with the resulting library of vectors, and expressing the genes under conditions in which detection of a desired activity, assembly into a trimeric molecules, binding to natural ligands, e.g., a receptor or substrates, facilitates relatively easy isolation of the vector encoding the gene whose product was detected. Each of the techniques described below is amenable to high throughput analysis for screening large numbers of sequences created, e.g., by random mutagenesis techniques.

Two Hybrid Systems

Two hybrid (interaction trap) assays can be used to identify a protein that interacts with corin. These may include, e.g., agonists, superagonists, and antagonists of corin. (The subject protein and a test protein it may interact with are used as the bait protein and prey proteins, respectively.) These assays rely on detecting the reconstitution of a functional transcriptional activator mediated by protein-protein interactions with a bait protein. In particular, these assays make use of chimeric genes that express hybrid proteins. The first hybrid comprises a DNA-binding domain fused to the bait protein, e.g., corin or active fragments thereof. The second hybrid protein contains a transcriptional activation domain fused to a "prey" protein, e.g. an expression library. If the prey and bait proteins are able to interact, they bring into close proximity the DNA-binding and transcriptional activator domains. This proximity is sufficient to cause transcription of a reporter gene that is operably linked to a transcriptional regulatory site that is recognized by the DNA binding domain, and expression of the marker gene can be detected and used to score for the interaction of the bait protein with another (prey) protein.

Display Libraries

In one approach to screening assays, the candidate peptides are displayed on the surface of a cell or viral particle, and the ability of particular cells or viral particles to bind an appropriate receptor protein via the displayed product is detected in a "panning assay". For example, the gene library can be cloned into the gene for a surface membrane protein of a bacterial cell, and the resulting fusion protein detected by panning (Ladner et al., WO 88/06630; Fuchs et al. (1991) *Bio/Technology* 9:1370-1371; and Goward et al. (1992) *TIBS* 18:136-140). This technique was used in Sahu et al. (1996) J. Immunology 157:884-891, to isolate a complement inhibitor. In a similar fashion, a detectably labeled ligand can be used to score for potentially functional peptide homologs. Fluorescently labeled ligands, e.g., receptors, can be used to detect homologs that retain ligand-binding activity. The use of fluorescently labeled ligands allows cells to be visually inspected and separated under a fluorescence microscope or, where the morphology of the cell permits, to be separated by a fluorescence-activated cell sorter.

A gene library can be expressed as a fusion protein on the surface of a viral particle. For instance, in the filamentous phage system, foreign peptide sequences can be expressed on the surface of infectious phage, thereby conferring two significant benefits. First, since these phage can be applied to affinity matrices at concentrations well over $10^{13}$ phage per milliliter, a large number of phage can be screened at one time. Second, since each infectious phage displays a gene product on its surface, if a particular phage is recovered from an affinity matrix in low yield, the phage can be amplified by another round of infection. The group of almost identical *E. coli* filamentous phages M13, fd., and f1 are most often used in phage display libraries. Either of the phage gIII or gVIII coat proteins can be used to generate fusion proteins without disrupting the ultimate packaging of the viral particle. Foreign epitopes can be expressed at the $NH_2$-terminal end of pIII and phage bearing such epitopes recovered from a large excess of phage lacking this epitope (Ladner et al., PCT publication WO 90/02909; Garrard et al., PCT publication WO 92/09690; Marks et al. (1992) *J. Biol. Chem.* 267:16007-16010; Griffiths et al. (1993) *EMBO J* 12:725-734; Clackson et al. (1991) *Nature* 352:624-628; and Barbas et al. (1992) *PNAS* 89:4457-4461).

A common approach uses the maltose receptor of *E. coli* (the outer membrane protein, LamB) as a peptide fusion partner (Charbit et al. (1986) *EMBO* 5:3029-3037). Oligonucleotides have been inserted into plasmids encoding the LamB gene to produce peptides fused into one of the extracellular loops of the protein. These peptides are available for binding to ligands, e.g., to antibodies, and can elicit an immune response when the cells are administered to animals. Other cell surface proteins, e.g., OmpA (Schorr et al. (1991) *Vaccines* 91:387-392), PhoE (Agterberg, et al. (1990) *Gene* 88:37-45), and PAL (Fuchs et al. (1991) *Bio/Tech* 9:1369-1372), as well as large bacterial surface structures have served as vehicles for peptide display. Peptides can be fused to pilin, a protein that polymerizes to form the pilus-a conduit for interbacterial exchange of genetic information (Thiry et al. (1989) *Appl. Environ. Microbiol.* 55:984-993). Because of its role in interacting with other cells, the pilus provides a useful support for the presentation of peptides to the extracellular environment. Another large surface structure used for peptide display is the bacterial motive organ, the flagellum. Fusion of peptides to the subunit protein flagellin offers a dense array of many peptide copies on the host cells (Kuwajima et al. (1988) *Bio/Tech.* 6:1080-1083). Surface proteins of other bacterial species have also served as peptide fusion partners. Examples include the *Staphylococcus* protein A and the outer membrane protease IgA of *Neisseria* (Hansson et al. (1992) *J. Bacteriol.* 174:4239-4245 and Klauser et al. (1990) *EMBO J.* 9:1991-1999).

In the filamentous phage systems and the LamB system described above, the physical link between the peptide and its encoding DNA occurs by the containment of the DNA within a particle (cell or phage) that carries the peptide on its surface. Capturing the peptide captures the particle and the DNA within.

The number of peptides that can be screened in recombinant random libraries is enormous. Libraries of $10^7$-$10^9$ independent clones are routinely prepared. Libraries as large as $10^{11}$ recombinants have been created. This limitation in library size occurs at the step of transforming the DNA containing randomized segments into the host bacterial cells. To circumvent this limitation, an in vitro system based on the display of nascent peptides in polysome complexes has recently been developed. This display library method has the potential of producing libraries 3-6 orders of magnitude larger than the currently available phage/phagemid or plasmid libraries. Furthermore, the construction of the libraries, expression of the peptides, and screening, is done in an entirely cell-free format.

In one application of this method (Gallop et al. (1994) *J. Med. Chem.* 37(9):1233-1251), a molecular DNA library encoding $10^{12}$ decapeptides was constructed and the library expressed in an *E. coli* S30 in vitro coupled transcription/translation system. Conditions were chosen to stall the ribosomes on the mRNA, causing the accumulation of a substantial proportion of the RNA in polysomes and yielding complexes containing nascent peptides still linked to their encoding RNA. The polysomes are sufficiently robust to be affinity purified on immobilized receptors in much the same way as the more conventional recombinant peptide display libraries are screened. RNA from the bound complexes is recovered, converted to cDNA, and amplified by PCR to produce a template for the next round of synthesis and screening. The polysome display method can be coupled to the phage display system. Following several rounds of screening, cDNA from the enriched pool of polysomes was cloned into a phagemid vector. This vector serves as both a peptide expression vector, displaying peptides fused to the coat proteins, and as a DNA sequencing vector for peptide identification. By expressing the polysome-derived peptides on phage, one can either continue the affinity selection procedure in this format or assay the peptides on individual clones for binding activity in a phage ELISA, or for binding specificity in a completion phage ELISA (Barret, et al. (1992) *Anal. Biochem* 204:357-364). To identify the sequences of the active peptides one sequences the DNA produced by the phagemid host.

Secondary Screens

The high throughput assays described above can be followed or substituted by secondary screens in order to identify biological activities that will, e.g., allow one skilled in the art to differentiate agonists from antagonists. The type of a secondary screen used will depend on the desired activity that needs to be tested. For example, a hair growth-related assay described herein can be used in which the ability to modulate, e.g., decrease or increase, or mimic corin activity in skin can be used to identify corin agonists and antagonists from a group of peptide fragments isolated through one of the primary screens described above.

Alternatively, a pro-ANP assay testing the ability of corin to process pro-ANP can be used to identify corin agonists and antagonists (see, e.g., Wu et al. (2002) J. Biol. Chem. 277: 16900-16905).

Peptide Mimetics

This disclosure also provides for production of the protein binding domains of corin, to generate mimetics, e.g. peptide or non-peptide agents, e.g., agonists.

Non-hydrolyzable peptide analogs of critical residues can be generated using benzodiazepine (e.g., see Freidinger et al. in Peptides: Chemistry and Biology, G. R. Marshall ed., ESCOM Publisher: Leiden, Netherlands, 1988), azepine (e.g., see Huffman et al. in Peptides: Chemistry and Biology, G. R. Marshall ed., ESCOM Publisher: Leiden, Netherlands, 1988), substituted gamma lactam rings (Garvey et al. in Peptides: Chemistry and Biology, G. R. Marshall ed., ESCOM Publisher: Leiden, Netherlands, 1988), keto-methylene pseudopeptides (Ewenson et al. (1986) J Med Chem 29:295; and Ewenson et al. in Peptides: Structure and Function (Proceedings of the 9th American Peptide Symposium) Pierce Chemical Co. Rockland, Ill., 1985), β-turn dipeptide cores (Nagai et al. (1985) Tetrahedron Lett 26:647; and Sato et al. (1986) J Chem Soc Perkin Trans 1:1231), and P-aminoalcohols (Gordon et al. (1985) Biochem Biophys Res Commun 126:419; and Dann et al. (1986) Biochem Biophys Res Commun 134:71).

EXAMPLES

Example 1

Anti-Corin Antibody Stains DP Cells in Mouse and Human

A series of expression constructs to express domains of the mouse corin (LRP4) protein in bacteria were constructed and used to generate peptides to raise anti-sera against the protein. Of six constructs tested, two gave stable peptides (denoted ALDL15 antigen, including LDL domains 1 through 5 of LRP4 (SEQ ID NO:4) and ALDL68 antigen, including LDL domains 6 through 8 of LRP4). These peptides were used to immunize rabbits in order to generate anti-sera. Other sizes and combinations of peptides (from any species, e.g., human or mouse) can also be used. For example, the entire extracellular domain of human or mouse corin can also be used.

Figure 2:
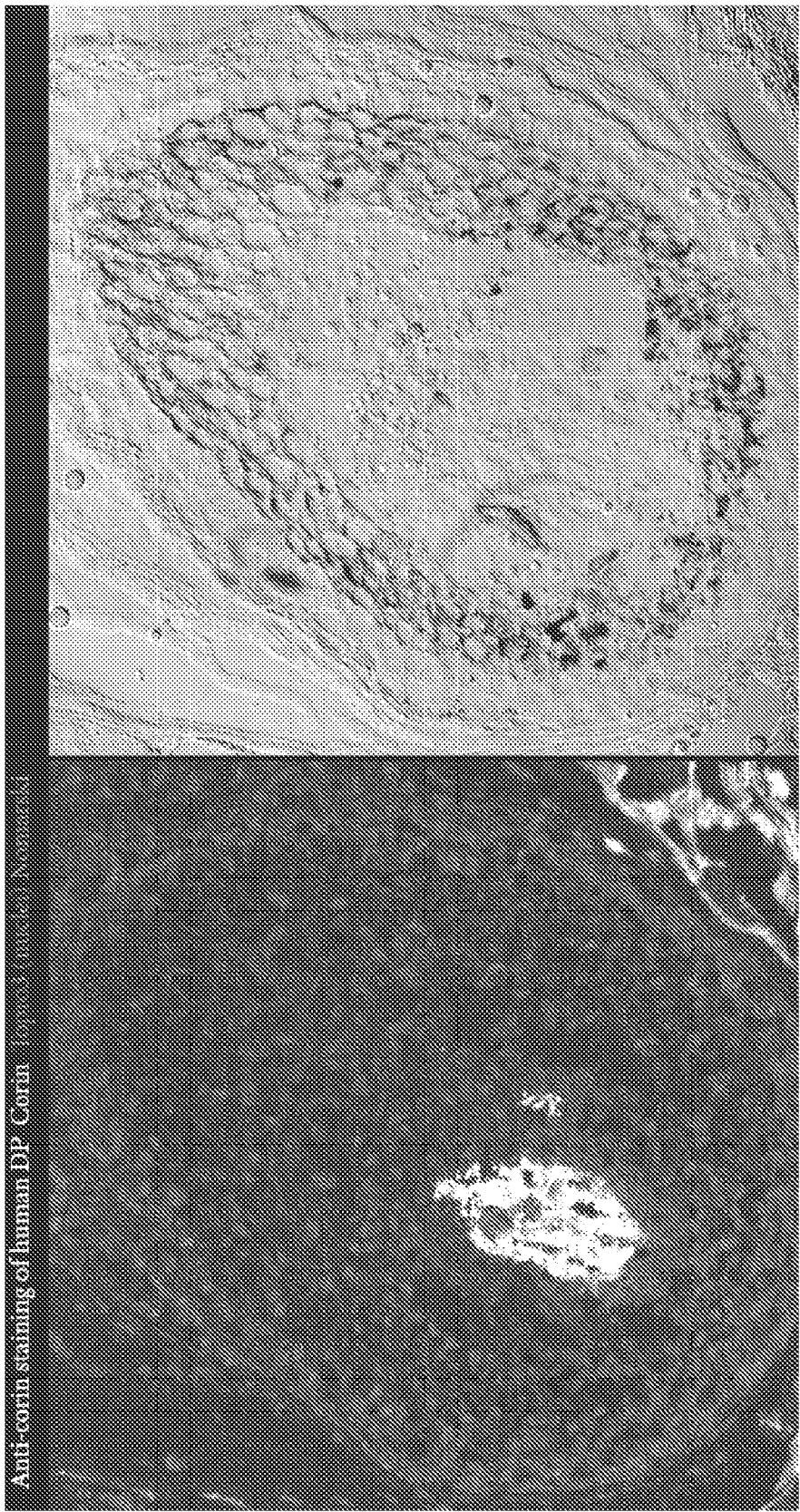
FIG. 2 is a micrograph of human skin stained with anti-LRP4 antibody.

The first set of anti-sera raised in rabbits showed that the ALDL15 expression construct was an effective immunogen. ALDL15 led to the production of anti-sera that specifically stained the dermal papilla in mouse skin by immunohistochemistry (FIG. 1). Immunohistochemistry on frozen sections of human skin confirmed that this protein is also expressed on the dermal papilla cells of human hair follicles and is not observed in other cell types in the skin (FIG. 2). These results demonstrate that corin is selectively expressed in DP cells of the skin in both mouse and human.

All publications and patents cited herein are hereby incorporated by reference. A number of embodiments have been described. Nevertheless, it will be understood that various modifications may be made without departing from the scope of the invention. Accordingly, other embodiments are within the scope of the following claims.

What is claimed is:

1. A method of identifying a dermal papilla (DP) cell, the method comprising providing a skin cell and detecting corin polypeptide expression by contacting the skin cell with an antibody or fragment thereof that specifically binds to a mouse corin consisting of the polypeptide sequence of SEQ ID NO:4 or human corin consisting of the polypeptide sequence of SEQ ID NO:1, wherein corin polypeptide expression identifies the skin cell as a DP cell.

2. The method of claim 1, wherein the antibody or fragment thereof comprises a label.

3. The method of claim 2, wherein the label is selected from the group consisting of a fluorescent tag, a radioactive tag, a myc tag, and a his tag.

4. The method of claim 1, wherein the step of detecting is performed in vitro.

5. The method of claim 1, further comprising isolating the DP cell.

6. The method of claim 1, wherein detecting corn expression comprises evaluating live cells.

7. The method of claim 1, wherein the antibody or fragment thereof binds specifically to a mouse corin consisting of the polypeptide sequence SEQ ID NO:4.

8. The method of claim 1, wherein the antibody or fragment thereof binds specifically to a human corin consisting of the polypeptide sequence SEQ ID NO:1.

9. The method of claim 1, wherein the skin cell is derived from a mammal.

10. The method of claim 1, wherein the skin cell is derived from a human.

* * * * *

SEQUENCE LISTING

```
<160> NUMBER OF SEQ ID NOS: 4

<210> SEQ ID NO 1
<211> LENGTH: 1042
<212> TYPE: PRT
<213> ORGANISM: Homo sapiens

<400> SEQUENCE: 1

Met Lys Gln Ser Pro Ala Leu Ala Pro Glu Glu Arg Tyr Arg Arg Ala
1               5                   10                  15
```

```
Gly Ser Pro Lys Pro Val Leu Arg Ala Asp Asp Asn Asn Met Gly Asn
         20                  25                  30

Gly Cys Ser Gln Lys Leu Ala Thr Ala Asn Leu Leu Arg Phe Leu Leu
         35                  40                  45

Leu Val Leu Ile Pro Cys Ile Cys Ala Leu Val Leu Leu Leu Val Ile
         50                  55                  60

Leu Leu Ser Tyr Val Gly Thr Leu Gln Lys Val Tyr Phe Lys Ser Asn
 65                  70                  75                  80

Gly Ser Glu Pro Leu Val Thr Asp Gly Glu Ile Gln Gly Ser Asp Val
                 85                  90                  95

Ile Leu Thr Asn Thr Ile Tyr Asn Gln Ser Thr Val Val Ser Thr Ala
                100                 105                 110

His Pro Asp Gln His Val Pro Ala Trp Thr Thr Asp Ala Ser Leu Pro
                115                 120                 125

Gly Asp Gln Ser His Arg Asn Thr Ser Ala Cys Met Asn Ile Thr His
130                 135                 140

Ser Gln Cys Gln Met Leu Pro Tyr His Ala Thr Leu Thr Pro Leu Leu
145                 150                 155                 160

Ser Val Val Arg Asn Met Glu Met Glu Lys Phe Leu Lys Phe Phe Thr
                165                 170                 175

Tyr Leu His Arg Leu Ser Cys Tyr Gln His Ile Met Leu Phe Gly Cys
                180                 185                 190

Thr Leu Ala Phe Pro Glu Cys Ile Ile Asp Gly Asp Ser His Gly
                195                 200                 205

Leu Leu Pro Cys Arg Ser Phe Cys Glu Ala Ala Lys Glu Gly Cys Glu
        210                 215                 220

Ser Val Leu Gly Met Val Asn Tyr Ser Trp Pro Asp Phe Leu Arg Cys
225                 230                 235                 240

Ser Gln Phe Arg Asn Gln Thr Glu Ser Ser Asn Val Ser Arg Ile Cys
                245                 250                 255

Phe Ser Pro Gln Gln Glu Asn Gly Lys Gln Leu Leu Cys Gly Arg Gly
                260                 265                 270

Glu Asn Phe Leu Cys Ala Ser Gly Ile Cys Ile Pro Gly Lys Leu Gln
                275                 280                 285

Cys Asn Gly Tyr Asn Asp Cys Asp Asp Trp Ser Asp Glu Ala His Cys
        290                 295                 300

Asn Cys Ser Glu Asn Leu Phe His Cys His Thr Gly Lys Cys Leu Asn
305                 310                 315                 320

Tyr Ser Leu Val Cys Asp Gly Tyr Asp Asp Cys Gly Asp Leu Ser Asp
                325                 330                 335

Glu Gln Asn Cys Asp Cys Asn Pro Thr Thr Glu His Arg Cys Gly Asp
                340                 345                 350

Gly Arg Cys Ile Ala Met Glu Trp Val Cys Asp Gly Asp His Asp Cys
        355                 360                 365

Val Asp Lys Ser Asp Glu Val Asn Cys Ser Cys His Ser Gln Gly Leu
        370                 375                 380

Val Glu Cys Arg Asn Gly Gln Cys Ile Pro Ser Thr Phe Gln Cys Asp
385                 390                 395                 400

Gly Asp Glu Asp Cys Lys Asp Gly Ser Asp Glu Glu Asn Cys Ser Val
                405                 410                 415

Ile Gln Thr Ser Cys Gln Glu Gly Asp Gln Arg Cys Leu Tyr Asn Pro
                420                 425                 430

Cys Leu Asp Ser Cys Gly Gly Ser Ser Leu Cys Asp Pro Asn Asn Ser
```

-continued

```
                435                 440                 445
Leu Asn Asn Cys Ser Gln Cys Glu Pro Ile Thr Leu Glu Leu Cys Met
    450                 455                 460
Asn Leu Pro Tyr Asn Ser Thr Ser Tyr Pro Asn Tyr Phe Gly His Arg
465                 470                 475                 480
Thr Gln Lys Glu Ala Ser Ile Ser Trp Glu Ser Ser Leu Phe Pro Ala
                485                 490                 495
Leu Val Gln Thr Asn Cys Tyr Lys Tyr Leu Met Phe Phe Ser Cys Thr
                500                 505                 510
Ile Leu Val Pro Lys Cys Asp Val Asn Thr Gly Glu Arg Ile Pro Pro
                515                 520                 525
Cys Arg Ala Leu Cys Glu His Ser Lys Glu Arg Cys Glu Ser Val Leu
    530                 535                 540
Gly Ile Val Gly Leu Gln Trp Pro Glu Asp Thr Asp Cys Ser Gln Phe
545                 550                 555                 560
Pro Glu Glu Asn Ser Asp Asn Gln Thr Cys Leu Met Pro Asp Glu Tyr
                565                 570                 575
Val Glu Glu Cys Ser Pro Ser His Phe Lys Cys Arg Ser Gly Gln Cys
            580                  585                 590
Val Leu Ala Ser Arg Arg Cys Asp Gly Gln Ala Asp Cys Asp Asp Asp
            595                  600                 605
Ser Asp Glu Glu Asn Cys Gly Cys Lys Glu Arg Asp Leu Trp Glu Cys
    610                 615                 620
Pro Ser Asn Lys Gln Cys Leu Lys His Thr Val Ile Cys Asp Gly Phe
625                 630                 635                 640
Pro Asp Cys Pro Asp Tyr Met Asp Glu Lys Asn Cys Ser Phe Cys Gln
                645                 650                 655
Asp Asp Glu Leu Glu Cys Ala Asn His Ala Cys Val Ser Arg Asp Leu
                660                 665                 670
Trp Cys Asp Gly Glu Ala Asp Cys Ser Asp Ser Ser Asp Glu Trp Asp
                675                 680                 685
Cys Val Thr Leu Ser Ile Asn Val Asn Ser Ser Phe Leu Met Val
    690                 695                 700
His Arg Ala Ala Thr Glu His His Val Cys Ala Asp Gly Trp Gln Glu
705                 710                 715                 720
Ile Leu Ser Gln Leu Ala Cys Lys Gln Met Gly Leu Gly Glu Pro Ser
                725                 730                 735
Val Thr Lys Leu Ile Gln Glu Gln Glu Lys Pro Arg Trp Leu Thr
                740                 745                 750
Leu His Ser Asn Trp Glu Ser Leu Asn Gly Thr Thr Leu His Glu Leu
    755                 760                 765
Leu Val Asn Gly Gln Ser Cys Glu Ser Arg Ser Lys Ile Ser Leu Leu
    770                 775                 780
Cys Thr Lys Gln Asp Cys Gly Arg Arg Pro Ala Ala Arg Met Asn Lys
785                 790                 795                 800
Arg Ile Leu Gly Gly Arg Thr Ser Arg Pro Gly Arg Trp Pro Trp Gln
                805                 810                 815
Cys Ser Leu Gln Ser Glu Pro Ser Gly His Ile Cys Gly Cys Val Leu
                820                 825                 830
Ile Ala Lys Lys Trp Val Leu Thr Val Ala His Cys Phe Glu Gly Arg
                835                 840                 845
Glu Asn Ala Ala Val Trp Lys Val Val Leu Gly Ile Asn Asn Leu Asp
                850                 855                 860
```

-continued

```
His Pro Ser Val Phe Met Gln Thr Arg Phe Val Lys Thr Ile Ile Leu
865                 870                 875                 880

His Pro Arg Tyr Ser Arg Ala Val Val Asp Tyr Asp Ile Ser Ile Val
            885                 890                 895

Glu Leu Ser Glu Asp Ile Ser Glu Thr Gly Tyr Val Arg Pro Val Cys
        900                 905                 910

Leu Pro Asn Pro Glu Gln Trp Leu Glu Pro Asp Thr Tyr Cys Tyr Ile
            915                 920                 925

Thr Gly Trp Gly His Met Gly Asn Lys Met Pro Phe Lys Leu Gln Glu
        930                 935                 940

Gly Glu Val Arg Ile Ile Ser Leu Glu His Cys Gln Ser Tyr Phe Asp
945                 950                 955                 960

Met Lys Thr Ile Thr Thr Arg Met Ile Cys Ala Gly Tyr Glu Ser Gly
                965                 970                 975

Thr Val Asp Ser Cys Met Gly Asp Ser Gly Gly Pro Leu Val Cys Glu
            980                 985                 990

Lys Pro Gly Gly Arg Trp Thr Leu Phe Gly Leu Thr Ser Trp Gly Ser
        995                 1000                1005

Val Cys Phe Ser Lys Val Leu Gly Pro Gly Val Tyr Ser Asn Val
    1010                1015                1020

Ser Tyr Phe Val Glu Trp Ile Lys Arg Gln Ile Tyr Ile Gln Thr
    1025                1030                1035

Phe Leu Leu Asn
    1040
```

<210> SEQ ID NO 2
<211> LENGTH: 1200
<212> TYPE: DNA
<213> ORGANISM: Homo sapiens
<220> FEATURE:
<221> NAME/KEY: Exon1
<222> LOCATION: (1001)..(1156)

<400> SEQUENCE: 2

```
tacatttgat ctcacttcag aaacaaaata ctgccccccc cattttacaa atgcatattt      60
ttttctcagc aataatgttc aagaacaagt gcttggccca tattttgttg tctttacatg     120
gctttcttta aataatgggg atggattat taaataacct catgagtaat tttcaaaatt     180
tccattaaga tcttgattga aattggatga aaaatcattt ctaagaaaaa cccaatgaag     240
tgttttcctt tgccacattt gacaattgcc ttggacttgg taaagtaatc attactgtgt     300
tgagtacctc cagtgccctc cttgacgctg ccttagaaaa ggtagctgct tttgaatgac     360
aggcaggaat ttgttcgcct tttaggttca gcctgtaggt gccctctgca ggaaatcagg     420
aactagggtt ttggaagcag tcagggtggg gttctccctt gtccctgcag cctcagcaaa     480
gactcaggca gtctggcaaa agcagttct tcagcatacc taacagaacg caagtttcca     540
tatgcctgat gcaaataatg gcctccaaac gttaaacctt ttttgagata aacttgttct     600
ttaattgcca gcgcctgcag ttaattttga ttggctacac tctggttaaa agaaaatgct     660
ttcgatgtga tatggcaaat ttggagaaaa gtaactcttt tgctcccaac cagtcttcca     720
caacttaaac ttaatcgtcc tgtccttttc tgctgccctc gtggagtgta agttttgag     780 ggagaccagc agaaactgac tttccatatg cccctgaaga ataacttctt tgaatgcaaa     840
gaggtgggga cacggaggat ctgtcattac gggttattat gggtgggacc cagagacggg     900
agtgaaggga gggtgtggcc cgcgggtggg atctgtagag cagacaaaat atggggcccc     960
```

-continued

```
tggcgcttaa agttcagttt gtctctcttg agcttggaga aaatcatccg tagtgcctcc    1020
ccgggggaca cgtagaggag agaaaagcga ccaagataaa agtggacaga agaataagcg    1080
agacttttta tccatgaaac agtctcctgc cctcgctccg gaagagcgct gccgcagagc    1140
cgggtcccca agccggtaa gatcgatgat tcgctgtcct accgcagcca ggtgtgatgg     1200
```

<210> SEQ ID NO 3
<211> LENGTH: 4804
<212> TYPE: DNA
<213> ORGANISM: Mus Musculus
<220> FEATURE:
<221> NAME/KEY: CDS
<222> LOCATION: (1)..(3339)

<400> SEQUENCE: 3

```
atg ggc agg gtt tcc ttc agc gtt cgg gtc agc tcc gtg cgg aga gcc      48
Met Gly Arg Val Ser Phe Ser Val Arg Val Ser Ser Val Arg Arg Ala
1               5                   10                  15 cgc tgc tct tgt cct ggg cga tgc tac ctc tcc tgc aga gtc cct cca      96
Arg Cys Ser Cys Pro Gly Arg Cys Tyr Leu Ser Cys Arg Val Pro Pro
                20                  25                  30 acc acc gcc ctc cgt gca ctg aac ggt ctt ggc tgc gcg ggg gtt ccg     144
Thr Thr Ala Leu Arg Ala Leu Asn Gly Leu Gly Cys Ala Gly Val Pro
            35                  40                  45 ggg gag act gca ggt gga gcc gtc gga ccc ggc ccc ttg ggg acc cgt     192
Gly Glu Thr Ala Gly Gly Ala Val Gly Pro Gly Pro Leu Gly Thr Arg
        50                  55                  60 ggc ttc ctc tcc ggg tcc aag ttc cag gct ccc ggc agc tgg aag gat     240
Gly Phe Leu Ser Gly Ser Lys Phe Gln Ala Pro Gly Ser Trp Lys Asp
65                  70                  75                  80 tgc ttt gga gcc ccg cct gct cca gac gtc ttg aga gca gac agg agc     288
Cys Phe Gly Ala Pro Pro Ala Pro Asp Val Leu Arg Ala Asp Arg Ser
                85                  90                  95 gtg ggc gag ggc tgt cct cag aag ctg gtg act gct aac ttg ctg cgc     336
Val Gly Glu Gly Cys Pro Gln Lys Leu Val Thr Ala Asn Leu Leu Arg
                100                 105                 110 ttc ctc ctg ctg gtg ctc atc ccc tgc atc tgc gcc ctc atc gtg ctg     384
Phe Leu Leu Leu Val Leu Ile Pro Cys Ile Cys Ala Leu Ile Val Leu
            115                 120                 125 ctg gcc atc ctg ctg tcc ttt gtg gga aca tta aaa agg gtt tat ttc     432
Leu Ala Ile Leu Leu Ser Phe Val Gly Thr Leu Lys Arg Val Tyr Phe
        130                 135                 140 aaa tca aat gac agt gaa cct ttg gtc act gat ggg gaa gct cga gtg     480
Lys Ser Asn Asp Ser Glu Pro Leu Val Thr Asp Gly Glu Ala Arg Val
145                 150                 155                 160 cct ggt gtt att cct gta aat aca gtt tat tat gag aac aca ggg gcg     528
Pro Gly Val Ile Pro Val Asn Thr Val Tyr Tyr Glu Asn Thr Gly Ala
                165                 170                 175 ccc tct ctg ccc ccc agc cag tcc act cca gcc tgg aca ccg aga gct     576
Pro Ser Leu Pro Pro Ser Gln Ser Thr Pro Ala Trp Thr Pro Arg Ala
            180                 185                 190 cct tct cca gag gac cag agt cac agg aac aca agc acc tgc atg aac     624
Pro Ser Pro Glu Asp Gln Ser His Arg Asn Thr Ser Thr Cys Met Asn
        195                 200                 205 atc act cac agc cag tgt caa att ctg ccc tac cac agc acg ttg gca     672
Ile Thr His Ser Gln Cys Gln Ile Leu Pro Tyr His Ser Thr Leu Ala
    210                 215                 220 cct ctc ttg cca att gtc aaa aac atg gac atg gag aag ttc ctc aag     720
Pro Leu Leu Pro Ile Val Lys Asn Met Asp Met Glu Lys Phe Leu Lys
225                 230                 235                 240
```

-continued

| | |
|---|---|
| ttc ttc acg tac ctc cat cgc ctc agt tgc tat caa cat atc ctg ctc<br>Phe Phe Thr Tyr Leu His Arg Leu Ser Cys Tyr Gln His Ile Leu Leu<br>            245                 250                 255 | 768 |
| ttc ggc tgt agc ctc gcc ttc cct gag tgc gtt gtt gat ggc gat gac<br>Phe Gly Cys Ser Leu Ala Phe Pro Glu Cys Val Val Asp Gly Asp Asp<br>        260                 265                 270 | 816 |
| agg cat ggt ctt cta ccc tgt aga tct ttc tgt gag gct gca aaa gaa<br>Arg His Gly Leu Leu Pro Cys Arg Ser Phe Cys Glu Ala Ala Lys Glu<br>            275                 280                 285 | 864 |
| gga tgc gaa tct gtc ctg gga atg gtg aac tcc tcc tgg ccg gat tcc<br>Gly Cys Glu Ser Val Leu Gly Met Val Asn Ser Ser Trp Pro Asp Ser<br>    290                 295                 300 | 912 |
| ctc aga tgc tct cag ttt agg gac cac act gag act aac agc agt gtc<br>Leu Arg Cys Ser Gln Phe Arg Asp His Thr Glu Thr Asn Ser Ser Val<br>305                 310                 315                 320 | 960 |
| aga aag agc tgc ttc tca ctg cag cag gaa cat gga aag caa tca ctc<br>Arg Lys Ser Cys Phe Ser Leu Gln Gln Glu His Gly Lys Gln Ser Leu<br>                325                 330                 335 | 1008 |
| tgt gga ggg ggc gag agc ttc ctg tgt acc agc ggg ctc tgc gtc ccc<br>Cys Gly Gly Gly Glu Ser Phe Leu Cys Thr Ser Gly Leu Cys Val Pro<br>            340                 345                 350 | 1056 |
| aag aag ctg cag tgt aac ggc tat aat gac tgt gat gac tgg agc gac<br>Lys Lys Leu Gln Cys Asn Gly Tyr Asn Asp Cys Asp Asp Trp Ser Asp<br>        355                 360                 365 | 1104 |
| gag gcg cat tgc aac tgc agc aag gat ctg ttt cac tgt ggc aca ggc<br>Glu Ala His Cys Asn Cys Ser Lys Asp Leu Phe His Cys Gly Thr Gly<br>    370                 375                 380 | 1152 |
| aag tgc ctc cac tac agc ctc ttg tgt gat ggg tac gat gac tgt ggg<br>Lys Cys Leu His Tyr Ser Leu Leu Cys Asp Gly Tyr Asp Asp Cys Gly<br>385                 390                 395                 400 | 1200 |
| gac ccg agt gac gag caa aac tgt gat tgt aat ctc aca aaa gag cat<br>Asp Pro Ser Asp Glu Gln Asn Cys Asp Cys Asn Leu Thr Lys Glu His<br>                405                 410                 415 | 1248 |
| cgc tgt gga gat ggg cgc tgc att gcg gct gag tgg gtg tgc gat ggg<br>Arg Cys Gly Asp Gly Arg Cys Ile Ala Ala Glu Trp Val Cys Asp Gly<br>            420                 425                 430 | 1296 |
| gac cat gac tgt gtg gac aag tct gat gag gtc aac tgc tct tgt cac<br>Asp His Asp Cys Val Asp Lys Ser Asp Glu Val Asn Cys Ser Cys His<br>        435                 440                 445 | 1344 |
| agc cag ggc ctg gtg gaa tgc aca agt gga cag tgc atc cct agc acc<br>Ser Gln Gly Leu Val Glu Cys Thr Ser Gly Gln Cys Ile Pro Ser Thr<br>    450                 455                 460 | 1392 |
| ttc cag tgt gat ggg gac gaa gac tgt aag gat ggg agt gac gag gag<br>Phe Gln Cys Asp Gly Asp Glu Asp Cys Lys Asp Gly Ser Asp Glu Glu<br>465                 470                 475                 480 | 1440 |
| aac tgc agt gac agt cag acg cca tgt cca gaa gga gaa cag gga tgc<br>Asn Cys Ser Asp Ser Gln Thr Pro Cys Pro Glu Gly Glu Gln Gly Cys<br>                485                 490                 495 | 1488 |
| ttt ggc agt tcc tgc gtc gaa tcc tgt gct ggt agc tct ctg tgt gac<br>Phe Gly Ser Ser Cys Val Glu Ser Cys Ala Gly Ser Ser Leu Cys Asp<br>            500                 505                 510 | 1536 |
| tca gac agc agc ctg agt aac tgc agt caa tgt gag ccc atc act ttg<br>Ser Asp Ser Ser Leu Ser Asn Cys Ser Gln Cys Glu Pro Ile Thr Leu<br>        515                 520                 525 | 1584 |
| gaa ctc tgc atg aat ttg ctc tac aac cat aca cat tat cca aat tac<br>Glu Leu Cys Met Asn Leu Leu Tyr Asn His Thr His Tyr Pro Asn Tyr<br>    530                 535                 540 | 1632 |
| ctt ggc cac aga act caa aag gaa gcg tcc atc agc tgg gag tca tcc<br>Leu Gly His Arg Thr Gln Lys Glu Ala Ser Ile Ser Trp Glu Ser Ser | 1680 |

-continued

```
           545                 550                 555                 560
ctt ttc cct gcc ctt gta caa acc aac tgt tac aaa tac ctc atg ttt              1728
Leu Phe Pro Ala Leu Val Gln Thr Asn Cys Tyr Lys Tyr Leu Met Phe
            565                 570                 575 ttc gct tgc acc att ttg gtt cca aag tgt gat gtg aat aca gga caa              1776
Phe Ala Cys Thr Ile Leu Val Pro Lys Cys Asp Val Asn Thr Gly Gln
        580                 585                 590 cgc atc ccg cct tgc aga ctc ctg tgt gag cac tcc aaa gag cgc tgt              1824
Arg Ile Pro Pro Cys Arg Leu Leu Cys Glu His Ser Lys Glu Arg Cys
            595                 600                 605 gag tct gtt ctg gga atc gtt ggc ctg cag tgg cct gaa gac acc gac              1872
Glu Ser Val Leu Gly Ile Val Gly Leu Gln Trp Pro Glu Asp Thr Asp
        610                 615                 620 tgc aat caa ttt cca gag gaa agt tca gac aat caa act tgc ctc ctg              1920
Cys Asn Gln Phe Pro Glu Glu Ser Ser Asp Asn Gln Thr Cys Leu Leu
625                 630                 635                 640 ccc aat gaa gat gtg gaa gaa tgc tct ccg agt cac ttc aaa tgc cgc              1968
Pro Asn Glu Asp Val Glu Glu Cys Ser Pro Ser His Phe Lys Cys Arg
                645                 650                 655 tcg gga cga tgc gtt ctg ggc tcc agg aga tgt gac ggc cag gct gac              2016
Ser Gly Arg Cys Val Leu Gly Ser Arg Arg Cys Asp Gly Gln Ala Asp
            660                 665                 670 tgt gac gac gac agt gac gag gag aac tgt ggt tgt aaa gag aga gct              2064
Cys Asp Asp Asp Ser Asp Glu Glu Asn Cys Gly Cys Lys Glu Arg Ala
        675                 680                 685 ctt tgg gaa tgt cca ttt aat aag caa tgt ctg aag cat aca tta atc              2112
Leu Trp Glu Cys Pro Phe Asn Lys Gln Cys Leu Lys His Thr Leu Ile
690                 695                 700 tgc gat ggg ttt cca gat tgt cca gac agt atg gat gaa aaa aac tgc              2160
Cys Asp Gly Phe Pro Asp Cys Pro Asp Ser Met Asp Glu Lys Asn Cys
705                 710                 715                 720 tca ttt tgc caa gac aat gag ctg gaa tgt gcc aac cat gag tgt gtg              2208
Ser Phe Cys Gln Asp Asn Glu Leu Glu Cys Ala Asn His Glu Cys Val
                725                 730                 735 ccg cgt gac ctt tgg tgc gac gga tgg gtc gac tgc tca gac agt tct              2256
Pro Arg Asp Leu Trp Cys Asp Gly Trp Val Asp Cys Ser Asp Ser Ser
            740                 745                 750 gat gaa tgg ggc tgt gtg acc ctc tct aaa aat ggg aac tcc tcc tca              2304
Asp Glu Trp Gly Cys Val Thr Leu Ser Lys Asn Gly Asn Ser Ser Ser
        755                 760                 765 ttg ctg act gtt cac aaa tct gca aag gaa cac cac gtg tgt gct gac              2352
Leu Leu Thr Val His Lys Ser Ala Lys Glu His His Val Cys Ala Asp
770                 775                 780 ggc tgg cgg gag acg ttg agt cag ctg gcc tgc aag cag atg ggt tta              2400
Gly Trp Arg Glu Thr Leu Ser Gln Leu Ala Cys Lys Gln Met Gly Leu
785                 790                 795                 800 gga gaa ccg tct gtg acc aag ctg atc cca gga cag gaa ggc cag cag              2448
Gly Glu Pro Ser Val Thr Lys Leu Ile Pro Gly Gln Glu Gly Gln Gln
                805                 810                 815 tgg ctg agg ttg tac ccc aac tgg gag aat ctc aat ggg agc acc ttg              2496
Trp Leu Arg Leu Tyr Pro Asn Trp Glu Asn Leu Asn Gly Ser Thr Leu
            820                 825                 830 cag gag ctg ctg gta tac agg cac tcc tgc cca agc aga agt gag att              2544
Gln Glu Leu Leu Val Tyr Arg His Ser Cys Pro Ser Arg Ser Glu Ile
        835                 840                 845 tcc ctt ctg tgc tcc aag caa gac tgt ggc cgc cgc cct gct gcc cga              2592
Ser Leu Leu Cys Ser Lys Gln Asp Cys Gly Arg Arg Pro Ala Ala Arg
850                 855                 860 atg aac aag agg atc ctt ggg ggt cgg act agt cgt cct ggg agg tgg              2640
```

```
                                -continued

Met Asn Lys Arg Ile Leu Gly Gly Arg Thr Ser Arg Pro Gly Arg Trp
865                 870                 875                 880 ccg tgg cag tgc tct ctg cag agt gaa ccc agt gga cat atc tgt ggc         2688
Pro Trp Gln Cys Ser Leu Gln Ser Glu Pro Ser Gly His Ile Cys Gly
                        885                 890                 895 tgt gtc ctc att gcc aag aag tgg gtc ctg aca gtt gcc cat tgc ttt         2736
Cys Val Leu Ile Ala Lys Lys Trp Val Leu Thr Val Ala His Cys Phe
                900                 905                 910 gaa ggg aga gaa gac gct gat gtt tgg aaa gtg gta ttt ggc ata aac         2784
Glu Gly Arg Glu Asp Ala Asp Val Trp Lys Val Val Phe Gly Ile Asn
            915                 920                 925 aac ctg gac cat cca tca ggc ttc atg cag acc cgc ttt gtg aag acc         2832
Asn Leu Asp His Pro Ser Gly Phe Met Gln Thr Arg Phe Val Lys Thr
        930                 935                 940 atc ctg cta cat ccc cgt tac agt cga gca gtg gta gac tat gat atc         2880
Ile Leu Leu His Pro Arg Tyr Ser Arg Ala Val Val Asp Tyr Asp Ile
945                 950                 955                 960 agc gtg gtg gag ctg agc gat gat atc aat gag aca agc tac gtc aga         2928
Ser Val Val Glu Leu Ser Asp Asp Ile Asn Glu Thr Ser Tyr Val Arg
                965                 970                 975 cct gtc tgc cta ccc agt ccg gag gag tat cta gaa cca gat acg tac         2976
Pro Val Cys Leu Pro Ser Pro Glu Glu Tyr Leu Glu Pro Asp Thr Tyr
            980                 985                 990 tgc tac atc aca ggc tgg ggc cac atg ggc aat aaa atg ccc ttt aag         3024
Cys Tyr Ile Thr Gly Trp Gly His Met Gly Asn Lys Met Pro Phe Lys
                995                 1000                1005 ctg cag gag gga gag gtc cgc att atc cct ctg gag cag tgc cag             3069
Leu Gln Glu Gly Glu Val Arg Ile Ile Pro Leu Glu Gln Cys Gln
    1010                1015                1020 tcc tat ttt gac atg aag acc atc acc aat cgg atg atc tgt gct             3114
Ser Tyr Phe Asp Met Lys Thr Ile Thr Asn Arg Met Ile Cys Ala
    1025                1030                1035 ggc tat gag tct ggc acc gtg gac tcc tgc atg gga gac agc ggt             3159
Gly Tyr Glu Ser Gly Thr Val Asp Ser Cys Met Gly Asp Ser Gly
    1040                1045                1050 ggg cct ctg gtt tgt gaa cga ccc gga gga cag tgg aca tta ttt             3204
Gly Pro Leu Val Cys Glu Arg Pro Gly Gly Gln Trp Thr Leu Phe
    1055                1060                1065 ggt tta act tca tgg ggc tcc gtc tgc ttt tcc aaa gtt ctg gga             3249
Gly Leu Thr Ser Trp Gly Ser Val Cys Phe Ser Lys Val Leu Gly
    1070                1075                1080 cct gga gtg tac agc aat gtg tct tac ttt gtg ggc tgg att gaa             3294
Pro Gly Val Tyr Ser Asn Val Ser Tyr Phe Val Gly Trp Ile Glu
    1085                1090                1095 aga caa ata tat atc cag acc ttt ctc caa aag aaa tcc caa gga             3339
Arg Gln Ile Tyr Ile Gln Thr Phe Leu Gln Lys Lys Ser Gln Gly
    1100                1105                1110 taatcagaga ctttgtgggg aaacctacat ggagaatgac cctctgaaac agaagcttgt       3399
cctgccaaga gctgtacgaa caggcgtttc acggacagga cgctcaacat gcaccgcaag       3459
atctctcctg tttgtgctag atgagtttta ctcaggcttt aatctctttc aacattatca      3519
tttattaatt tcatgaatcc ttttaaaagc acagagcaaa gtaggttttg ttattttgct      3579
aggctaacct tgaatgtagt gtgcaattac caacccatag agacatttgg agctctaggg      3639
taacaagtta tagaaagctc cttttattac tactacaaga cacacacgga gatacacgct      3699
gactgatctc cagtttctgc ttaagcccag tggcttaggg ggcacatttc agaactgatc      3759
ttggagactg gcttttaatt tgtagaaagc caagagaata tatatgcttt tattatttac     3819
```

-continued

```
tctactcttc taaataactt gaagaaatca tgaaagacag agaaaggacc cacagtgttg    3879
atctagacag ttgaagttgc aagaatgtaa aattctctag ccaaccaaac taacactctg    3939
aagtaagtag aattctatcc tttctgtatt caaattaagc ttaaaatctc caccagattt    3999
gttcccgtta ctgggaattt tcggagtatg tcacttagat gactgtgatg tcaaaagcca    4059
ggtcaatcct tgaggaaata atttgtttgc ttatgtggga atgaataaga atctttccat    4119
tccgcaaaac acacaaatta aaaggagaa aaaaaattaa ataacattcc acacccaatt    4179
aattctgaaa attagtctgc ttgtattcac ccaaaacaga aaagttacag aaatatattt    4239
caaagtgcag caaaatgttg catggagtat ataacatttt gcaatttccc cctcatgatg    4299
tctaacatcc ggtattgcca tttgcctcat tgataattaa aactaaattt taaggatgct    4359
tttaagcact gggccacttt atgggaatca attcccaaag caattagtgg ttacaagtat    4419 ttttcccac taaaaagttt caaaacacaa accttcatac taaattaatt agccagacat    4479
gaactatgta acatgcaaat gccttttga acaagtagga tgcactgtta aacttccacca    4539 gcaaccaaac tgcctcagta ttgcttacag ggactacctg caattttata tgtgtatttt    4599
gtactctttt tctagatagt tcaaatgcaa aacattgttt caaccccat tctccatgtt    4659 gttcacctct tgtcctggaa tttgttacaa agtgtgtgta gcaaatgatt gtactgcggt    4719
caggactata tgaaggttta ggaccatcgg gtcggttttg ttataattgt tggcacataa    4779
ttaataaaat attttttagca ttggg                                        4804
```

<210> SEQ ID NO 4
<211> LENGTH: 1113
<212> TYPE: PRT
<213> ORGANISM: Mus Musculus

<400> SEQUENCE: 4

```
Met Gly Arg Val Ser Phe Ser Val Arg Val Ser Val Arg Arg Ala
1               5                   10                  15

Arg Cys Ser Cys Pro Gly Arg Cys Tyr Leu Ser Cys Arg Val Pro Pro
            20                  25                  30

Thr Thr Ala Leu Arg Ala Leu Asn Gly Leu Gly Cys Ala Gly Val Pro
        35                  40                  45

Gly Glu Thr Ala Gly Gly Ala Val Gly Pro Gly Pro Leu Gly Thr Arg
    50                  55                  60

Gly Phe Leu Ser Gly Ser Lys Phe Gln Ala Pro Gly Ser Trp Lys Asp
65                  70                  75                  80

Cys Phe Gly Ala Pro Ala Pro Asp Val Leu Arg Ala Asp Arg Ser
                85                  90                  95

Val Gly Glu Gly Cys Pro Gln Lys Leu Val Thr Ala Asn Leu Leu Arg
            100                 105                 110

Phe Leu Leu Leu Val Leu Ile Pro Cys Ile Cys Ala Leu Ile Val Leu
        115                 120                 125

Leu Ala Ile Leu Leu Ser Phe Val Gly Thr Leu Lys Arg Val Tyr Phe
    130                 135                 140

Lys Ser Asn Asp Ser Glu Pro Leu Val Thr Asp Gly Glu Ala Arg Val
145                 150                 155                 160

Pro Gly Val Ile Pro Val Asn Thr Val Tyr Tyr Glu Asn Thr Gly Ala
                165                 170                 175

Pro Ser Leu Pro Pro Ser Gln Ser Thr Pro Ala Trp Thr Pro Arg Ala
            180                 185                 190

Pro Ser Pro Glu Asp Gln Ser His Arg Asn Thr Ser Thr Cys Met Asn
```

-continued

```
            195                 200                 205
Ile Thr His Ser Gln Cys Gln Ile Leu Pro Tyr His Ser Thr Leu Ala
210                 215                 220
Pro Leu Leu Pro Ile Val Lys Asn Met Asp Met Glu Lys Phe Leu Lys
225                 230                 235                 240
Phe Phe Thr Tyr Leu His Arg Leu Ser Cys Tyr Gln His Ile Leu Leu
                245                 250                 255
Phe Gly Cys Ser Leu Ala Phe Pro Glu Cys Val Val Asp Gly Asp Asp
                260                 265                 270
Arg His Gly Leu Leu Pro Cys Arg Ser Phe Cys Glu Ala Ala Lys Glu
                275                 280                 285
Gly Cys Glu Ser Val Leu Gly Met Val Asn Ser Ser Trp Pro Asp Ser
290                 295                 300
Leu Arg Cys Ser Gln Phe Arg Asp His Thr Glu Thr Asn Ser Ser Val
305                 310                 315                 320
Arg Lys Ser Cys Phe Ser Leu Gln Gln Glu His Gly Lys Gln Ser Leu
                325                 330                 335
Cys Gly Gly Glu Ser Phe Leu Cys Thr Ser Gly Leu Cys Val Pro
                340                 345                 350
Lys Lys Leu Gln Cys Asn Gly Tyr Asn Asp Cys Asp Asp Trp Ser Asp
                355                 360                 365
Glu Ala His Cys Asn Cys Ser Lys Asp Leu Phe His Cys Gly Thr Gly
                370                 375                 380
Lys Cys Leu His Tyr Ser Leu Leu Cys Asp Gly Tyr Asp Asp Cys Gly
385                 390                 395                 400
Asp Pro Ser Asp Glu Gln Asn Cys Asp Cys Asn Leu Thr Lys Glu His
                405                 410                 415
Arg Cys Gly Asp Gly Arg Cys Ile Ala Ala Glu Trp Val Cys Asp Gly
                420                 425                 430
Asp His Asp Cys Val Asp Lys Ser Asp Glu Val Asn Cys Ser Cys His
                435                 440                 445
Ser Gln Gly Leu Val Glu Cys Thr Ser Gly Gln Cys Ile Pro Ser Thr
450                 455                 460
Phe Gln Cys Asp Gly Asp Glu Asp Cys Lys Asp Gly Ser Asp Glu Glu
465                 470                 475                 480
Asn Cys Ser Asp Ser Gln Thr Pro Cys Pro Glu Gly Glu Gln Gly Cys
                485                 490                 495
Phe Gly Ser Ser Cys Val Glu Ser Cys Ala Gly Ser Ser Leu Cys Asp
                500                 505                 510
Ser Asp Ser Ser Leu Ser Asn Cys Ser Gln Cys Glu Pro Ile Thr Leu
                515                 520                 525
Glu Leu Cys Met Asn Leu Leu Tyr Asn His Thr His Tyr Pro Asn Tyr
                530                 535                 540
Leu Gly His Arg Thr Gln Lys Glu Ala Ser Ile Ser Trp Glu Ser Ser
545                 550                 555                 560
Leu Phe Pro Ala Leu Val Gln Thr Asn Cys Tyr Lys Tyr Leu Met Phe
                565                 570                 575
Phe Ala Cys Thr Ile Leu Val Pro Lys Cys Asp Val Asn Thr Gly Gln
                580                 585                 590
Arg Ile Pro Pro Cys Arg Leu Leu Cys Glu His Ser Lys Glu Arg Cys
                595                 600                 605
Glu Ser Val Leu Gly Ile Val Gly Leu Gln Trp Pro Glu Asp Thr Asp
610                 615                 620
```

```
Cys Asn Gln Phe Pro Glu Glu Ser Ser Asp Asn Gln Thr Cys Leu Leu
625                 630                 635                 640

Pro Asn Glu Asp Val Glu Glu Cys Ser Pro Ser His Phe Lys Cys Arg
            645                 650                 655

Ser Gly Arg Cys Val Leu Gly Ser Arg Arg Cys Asp Gly Gln Ala Asp
            660                 665                 670

Cys Asp Asp Asp Ser Asp Glu Glu Asn Cys Gly Cys Lys Glu Arg Ala
            675                 680                 685

Leu Trp Glu Cys Pro Phe Asn Lys Gln Cys Leu Lys His Thr Leu Ile
        690                 695                 700

Cys Asp Gly Phe Pro Asp Cys Pro Asp Ser Met Asp Glu Lys Asn Cys
705                 710                 715                 720

Ser Phe Cys Gln Asp Asn Glu Leu Glu Cys Ala Asn His Glu Cys Val
                725                 730                 735

Pro Arg Asp Leu Trp Cys Asp Gly Trp Val Asp Cys Ser Asp Ser Ser
                740                 745                 750

Asp Glu Trp Gly Cys Val Thr Leu Ser Lys Asn Gly Asn Ser Ser Ser
            755                 760                 765

Leu Leu Thr Val His Lys Ser Ala Lys Glu His His Val Cys Ala Asp
        770                 775                 780

Gly Trp Arg Glu Thr Leu Ser Gln Leu Ala Cys Lys Gln Met Gly Leu
785                 790                 795                 800

Gly Glu Pro Ser Val Thr Lys Leu Ile Pro Gly Gln Glu Gly Gln Gln
                805                 810                 815

Trp Leu Arg Leu Tyr Pro Asn Trp Glu Asn Leu Asn Gly Ser Thr Leu
                820                 825                 830

Gln Glu Leu Leu Val Tyr Arg His Ser Cys Pro Ser Arg Ser Glu Ile
            835                 840                 845

Ser Leu Leu Cys Ser Lys Gln Asp Cys Gly Arg Arg Pro Ala Ala Arg
        850                 855                 860

Met Asn Lys Arg Ile Leu Gly Gly Arg Thr Ser Arg Pro Gly Arg Trp
865                 870                 875                 880

Pro Trp Gln Cys Ser Leu Gln Ser Glu Pro Ser Gly His Ile Cys Gly
                885                 890                 895

Cys Val Leu Ile Ala Lys Lys Trp Val Leu Thr Val Ala His Cys Phe
                900                 905                 910

Glu Gly Arg Glu Asp Ala Asp Val Trp Lys Val Val Phe Gly Ile Asn
            915                 920                 925

Asn Leu Asp His Pro Ser Gly Phe Met Gln Thr Arg Phe Val Lys Thr
    930                 935                 940

Ile Leu Leu His Pro Arg Tyr Ser Arg Ala Val Val Asp Tyr Asp Ile
945                 950                 955                 960

Ser Val Val Glu Leu Ser Asp Asp Ile Asn Glu Thr Ser Tyr Val Arg
                965                 970                 975

Pro Val Cys Leu Pro Ser Pro Glu Glu Tyr Leu Glu Pro Asp Thr Tyr
            980                 985                 990

Cys Tyr Ile Thr Gly Trp Gly His Met Gly Asn Lys Met Pro Phe Lys
        995                 1000                1005

Leu Gln Glu Gly Glu Val Arg Ile Ile Pro Leu Glu Gln Cys Gln
    1010                1015                1020

Ser Tyr Phe Asp Met Lys Thr Ile Thr Asn Arg Met Ile Cys Ala
    1025                1030                1035
```

-continued

```
Gly Tyr Glu Ser Gly Thr Val Asp Ser Cys Met Gly Asp Ser Gly
    1040            1045                1050

Gly Pro Leu Val Cys Glu Arg Pro Gly Gly Gln Trp Thr Leu Phe
    1055            1060                1065

Gly Leu Thr Ser Trp Gly Ser Val Cys Phe Ser Lys Val Leu Gly
    1070            1075                1080

Pro Gly Val Tyr Ser Asn Val Ser Tyr Phe Val Gly Trp Ile Glu
    1085            1090                1095

Arg Gln Ile Tyr Ile Gln Thr Phe Leu Gln Lys Lys Ser Gln Gly
    1100            1105                1110
```